United States Patent
Howard et al.

(10) Patent No.: US 7,641,992 B2
(45) Date of Patent: Jan. 5, 2010

(54) MEDICAL DEVICE HAVING LITHIUM-ION BATTERY

(75) Inventors: William G. Howard, Roseville, MN (US); Craig L. Schmidt, Eagan, MN (US); Erik R. Scott, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 684 days.

(21) Appl. No.: 10/978,970

(22) Filed: Oct. 29, 2004

(65) Prior Publication Data

US 2006/0093872 A1    May 4, 2006

(51) Int. Cl.
*H01M 12/00* (2006.01)
*H01M 14/00* (2006.01)
*H01M 6/36* (2006.01)
*A61N 1/00* (2006.01)

(52) U.S. Cl. .............................. 429/9; 429/7; 429/117; 607/29

(58) Field of Classification Search ................. 429/117, 429/231.95, 7, 8, 19, 231.8, 9; 607/29
See application file for complete search history.

(56) References Cited

U.S. PATENT DOCUMENTS

| | | | |
|---|---|---|---|
| 3,791,867 A | 2/1974 | Broadhead et al. |
| 3,864,167 A | 2/1975 | Broadhead et al. |
| 3,898,096 A | 8/1975 | Heredy et al. |
| 4,009,052 A | 2/1977 | Whittingham |
| 4,048,397 A | 9/1977 | Rothbauer |
| 4,049,887 A | 9/1977 | Whittingham |
| 4,113,921 A | 9/1978 | Goldstein et al. |
| 4,194,062 A | 3/1980 | Carides et al. |
| 4,202,702 A | 5/1980 | Nuss |
| 4,340,652 A | 7/1982 | Raistrick et al. |
| 4,446,212 A | 5/1984 | Kaun |
| 4,464,447 A | 8/1984 | Lazzari et al. |

(Continued)

FOREIGN PATENT DOCUMENTS

EP    0 567 149 B1    10/1993

(Continued)

OTHER PUBLICATIONS

International Search Report for PCT/US2005/038942, date of mailing, Mar. 2, 2006, 3 pages.

(Continued)

*Primary Examiner*—Dah-Wei D Yuan
*Assistant Examiner*—Maria J Laios
(74) *Attorney, Agent, or Firm*—Scott A. Marks; Stephen W. Bauer

(57) ABSTRACT

A medical device includes a rechargeable lithium-ion battery for providing power to the medical device. The lithium-ion battery includes a positive electrode including a current collector and a first active material, a negative electrode including a current collector and a second active material, and an auxiliary electrode including a current collector and a third active material. The auxiliary electrode is configured for selective electrical connection to one of the positive electrode and the negative electrode. The first active material, second active material, and third active material are configured to allow doping and undoping of lithium ions. The third active material exhibits charging and discharging capacity below a corrosion potential of the current collector of the negative electrode and above a decomposition potential of the first active material.

76 Claims, 11 Drawing Sheets

U.S. PATENT DOCUMENTS

| | | | |
|---|---|---|---|
| 4,507,371 | A | 3/1985 | Thackeray et al. |
| 4,547,442 | A | 10/1985 | Besenhard et al. |
| 4,555,456 | A | 11/1985 | Kanehori et al. |
| 4,668,595 | A | 5/1987 | Yoshino et al. |
| 4,764,437 | A | 8/1988 | Kaun |
| 4,830,939 | A | 5/1989 | Lee et al. |
| H723 | H | 1/1990 | Plichta et al. |
| 5,053,297 | A | 10/1991 | Yamahira et al. |
| 5,077,151 | A | 12/1991 | Yasuda et al. |
| 5,147,737 | A | 9/1992 | Post et al. |
| 5,147,739 | A | 9/1992 | Beard |
| 5,160,712 | A | 11/1992 | Thackeray et al. |
| 5,162,170 | A | 11/1992 | Miyabayashi et al. |
| 5,169,736 | A | 12/1992 | Bittihn et al. |
| 5,176,969 | A | 1/1993 | Miyabayashi et al. |
| 5,187,033 | A | 2/1993 | Koshiba |
| 5,187,035 | A | 2/1993 | Miyabayashi et al. |
| 5,196,279 | A | 3/1993 | Tarascon |
| 5,264,201 | A | 11/1993 | Dahn et al. |
| 5,284,721 | A | 2/1994 | Beard |
| 5,296,318 | A | 3/1994 | Gozdz et al. |
| 5,300,373 | A | 4/1994 | Shackle |
| 5,322,746 | A | 6/1994 | Wainwright |
| 5,340,666 | A | 8/1994 | Tomantschger et al. |
| 5,401,598 | A | 3/1995 | Miyabayashi et al. |
| 5,411,537 | A | 5/1995 | Munshi et al. |
| 5,418,090 | A | 5/1995 | Koksbang et al. |
| 5,498,489 | A | 3/1996 | Dasgupta et al. |
| 5,510,212 | A | 4/1996 | Delnick et al. |
| 5,525,441 | A | 6/1996 | Reddy et al. |
| 5,545,468 | A | 8/1996 | Koshiba et al. |
| 5,547,785 | A | 8/1996 | Yumiba et al. |
| 5,569,553 | A | 10/1996 | Smesko et al. |
| 5,576,608 | A | 11/1996 | Nagai et al. |
| 5,652,072 | A | 7/1997 | Lamanna et al. |
| 5,670,862 | A | 9/1997 | Lewyn |
| 5,691,081 | A | 11/1997 | Krause et al. |
| 5,744,264 | A | 4/1998 | Barker |
| 5,776,628 | A | 7/1998 | Kraft et al. |
| 5,882,218 | A | 3/1999 | Reimers |
| 5,888,665 | A | 3/1999 | Bugga et al. |
| 5,911,947 | A | 6/1999 | Mitchell |
| 5,935,724 | A | 8/1999 | Spillman et al. |
| 5,935,728 | A | 8/1999 | Spillman et al. |
| 5,968,681 | A | 10/1999 | Miura et al. |
| 6,001,507 | A | 12/1999 | Ono et al. |
| 6,007,947 | A | 12/1999 | Mayer |
| 6,025,093 | A | 2/2000 | Herr |
| 6,060,186 | A * | 5/2000 | Broussely ............... 429/7 |
| 6,120,938 | A | 9/2000 | Atsumi et al. |
| 6,139,815 | A | 10/2000 | Atsumi et al. |
| 6,165,638 | A | 12/2000 | Spillman et al. |
| 6,171,729 | B1 | 1/2001 | Gan et al. |
| 6,203,947 | B1 | 3/2001 | Peled et al. |
| 6,203,994 | B1 | 3/2001 | Epps et al. |
| 6,207,327 | B1 | 3/2001 | Takada et al. |
| 6,221,531 | B1 | 4/2001 | Vaughey et al. |
| 6,228,536 | B1 | 5/2001 | Wasynczuk |
| 6,258,473 | B1 | 7/2001 | Spillman et al. |
| 6,265,100 | B1 | 7/2001 | Saaski et al. |
| 6,274,271 | B1 | 8/2001 | Koshiba et al. |
| 6,287,721 | B1 | 9/2001 | Xie et al. |
| 6,316,145 | B1 | 11/2001 | Kida et al. |
| 6,335,115 | B1 * | 1/2002 | Meissner ............... 429/117 |
| 6,372,384 | B1 | 4/2002 | Fujimoto et al. |
| 6,379,842 | B1 | 4/2002 | Mayer |
| 6,451,480 | B1 | 9/2002 | Gustafson et al. |
| 6,453,198 | B1 * | 9/2002 | Torgerson et al. ......... 607/29 |
| 6,461,751 | B1 | 10/2002 | Boehm et al. |
| 6,461,757 | B1 | 10/2002 | Sasayama et al. |
| 6,475,673 | B1 | 11/2002 | Yamawaki et al. |
| 6,489,062 | B1 | 12/2002 | Watanabe |
| 6,528,208 | B1 | 3/2003 | Thackeray et al. |
| 6,553,263 | B1 | 4/2003 | Meadows et al. |
| 6,596,439 | B1 | 7/2003 | Tsukamoto et al. |
| 6,645,675 | B1 | 11/2003 | Munshi |
| 6,677,083 | B2 | 1/2004 | Suzuki et al. |
| 6,706,445 | B2 | 3/2004 | Barker et al. |
| 6,720,112 | B2 | 4/2004 | Barker et al. |
| 6,730,437 | B2 | 5/2004 | Leising et al. |
| 6,737,191 | B2 | 5/2004 | Gan et al. |
| 6,759,168 | B2 | 7/2004 | Yamasaki et al. |
| 6,761,744 | B1 | 7/2004 | Tsukamoto et al. |
| 6,777,132 | B2 | 8/2004 | Barker et al. |
| 6,824,920 | B1 | 11/2004 | Iwamoto et al. |
| 6,849,360 | B2 | 2/2005 | Marple |
| 6,942,949 | B2 | 9/2005 | Besenhard et al. |
| 7,029,793 | B2 | 4/2006 | Nakagawa et al. |
| 7,101,642 | B2 | 9/2006 | Tsukamoto et al. |
| 7,157,185 | B2 | 1/2007 | Marple |
| 7,191,008 | B2 | 3/2007 | Schmidt et al. |
| 7,211,350 | B2 | 5/2007 | Amatucci |
| 7,337,010 | B2 | 2/2008 | Howard et al. |
| 7,459,235 | B2 | 12/2008 | Choi et al. |
| 2001/0008725 | A1 | 7/2001 | Howard |
| 2001/0012590 | A1 | 8/2001 | Ehrlich |
| 2001/0021472 | A1 | 9/2001 | Barker et al. |
| 2001/0031401 | A1 | 10/2001 | Yamawaki et al. |
| 2003/0025482 | A1 | 2/2003 | Tsukamoto et al. |
| 2003/0104282 | A1 | 6/2003 | Xing et al. |
| 2003/0157410 | A1 | 8/2003 | Jarvis et al. |
| 2003/0215716 | A1 * | 11/2003 | Suzuki et al. ............... 429/232 |
| 2004/0023117 | A1 * | 2/2004 | Imachi et al. .......... 429/231.95 |
| 2004/0096745 | A1 | 5/2004 | Shibano et al. |
| 2004/0147971 | A1 | 7/2004 | Greatbatch et al. |
| 2004/0147972 | A1 | 7/2004 | Greatbatch et al. |
| 2004/0158296 | A1 | 8/2004 | Greatbatch et al. |
| 2004/0168307 | A1 | 9/2004 | Hong |
| 2004/0176818 | A1 | 9/2004 | Wahlstrand et al. |
| 2004/0197657 | A1 | 10/2004 | Spitler et al. |
| 2005/0031919 | A1 * | 2/2005 | Ovshinsky et al. ............ 429/19 |
| 2005/0069777 | A1 | 3/2005 | Takami et al. |
| 2005/0130043 | A1 * | 6/2005 | Gao et al. .............. 429/231.95 |
| 2005/0147889 | A1 | 7/2005 | Ohzuku et al. |
| 2005/0164082 | A1 | 7/2005 | Kishi et al. |
| 2005/0244716 | A1 | 11/2005 | Ogawa et al. |
| 2006/0024582 | A1 | 2/2006 | Li et al. |
| 2006/0046149 | A1 | 3/2006 | Yong et al. |
| 2006/0068282 | A1 | 3/2006 | Kishi et al. |
| 2006/0093871 | A1 | 5/2006 | Howard et al. |
| 2006/0093872 | A1 | 5/2006 | Howard et al. |
| 2006/0093873 | A1 | 5/2006 | Howard et al. |
| 2006/0093894 | A1 | 5/2006 | Scott et al. |
| 2006/0093913 | A1 | 5/2006 | Howard et al. |
| 2006/0093916 | A1 | 5/2006 | Howard et al. |
| 2006/0093917 | A1 | 5/2006 | Howard et al. |
| 2006/0093918 | A1 | 5/2006 | Howard et al. |
| 2006/0093921 | A1 | 5/2006 | Scott et al. |
| 2006/0093923 | A1 | 5/2006 | Howard et al. |
| 2006/0095094 | A1 | 5/2006 | Howard et al. |
| 2006/0216612 | A1 | 9/2006 | Jambunathan et al. |
| 2006/0234125 | A1 | 10/2006 | Valle |
| 2006/0251968 | A1 | 11/2006 | Tsukamoto et al. |
| 2007/0009801 | A1 | 1/2007 | Inagaki et al. |
| 2007/0059587 | A1 | 3/2007 | Kishi et al. |
| 2007/0072085 | A1 | 3/2007 | Chen et al. |
| 2007/0077496 | A1 | 4/2007 | Scott et al. |
| 2007/0111099 | A1 | 5/2007 | Nanjundaswamy et al. |
| 2007/0134556 | A1 | 6/2007 | Sano et al. |
| 2007/0162083 | A1 | 7/2007 | Schmidt et al. |
| 2007/0233195 | A1 | 10/2007 | Wahlstrand et al. |
| 2007/0239221 | A1 | 10/2007 | Kast et al. |
| 2007/0248881 | A1 | 10/2007 | Scott et al. |
| 2007/0284159 | A1 | 12/2007 | Takami et al. |

| | | | |
|---|---|---|---|
| 2008/0020278 A1 | 1/2008 | Schmidt et al. | |
| 2008/0020279 A1 | 1/2008 | Schmidt et al. | |
| 2008/0026297 A1 | 1/2008 | Chen et al. | |
| 2008/0044728 A1 | 2/2008 | Schmidt et al. | |
| 2009/0035662 A1 | 2/2009 | Scott et al. | |

FOREIGN PATENT DOCUMENTS

| | | |
|---|---|---|
| EP | 0 732 761 A2 | 9/1996 |
| EP | 0 982 790 A1 | 3/2000 |
| EP | 1 014 465 A1 | 6/2000 |
| EP | 1 018 773 A1 | 7/2000 |
| EP | 1 069 635 A1 | 1/2001 |
| EP | 1 282 180 A1 | 2/2003 |
| EP | 1 487 039 A1 | 12/2004 |
| EP | 1 722 439 A1 | 11/2006 |
| JP | 56-136462 | 10/1981 |
| JP | 57-11476 | 1/1982 |
| JP | 63-1708 | 1/1982 |
| JP | 57-152669 | 9/1982 |
| JP | 02-309568 | 12/1990 |
| JP | 6-275263 | 9/1994 |
| JP | 10-027626 A | 1/1998 |
| JP | 2000156229 A | 6/2000 |
| JP | 2000-195499 A | 7/2000 |
| JP | 2001-126756 A | 5/2001 |
| JP | 2001-185141 A | 7/2001 |
| WO | WO 97/06569 A1 | 2/1997 |
| WO | WO 97/48141 | 12/1997 |
| WO | WO 00/017950 | 3/2000 |
| WO | WO 02/09215 A2 | 1/2002 |
| WO | WO 02/21628 A1 | 3/2002 |
| WO | WO 02/069414 A2 | 9/2002 |
| WO | WO 02/095845 A1 | 11/2002 |
| WO | WO 03/044880 A1 | 5/2003 |
| WO | WO 03/075371 A2 | 9/2003 |
| WO | WO 03/090293 A2 | 10/2003 |
| WO | WO 2006/050022 A2 | 5/2006 |
| WO | WO 2006/050023 A2 | 5/2006 |
| WO | WO 2006/050098 A1 | 5/2006 |
| WO | WO 2006/050099 A1 | 5/2006 |
| WO | WO 2006/050100 A2 | 5/2006 |
| WO | WO 2006/050117 A1 | 5/2006 |
| WO | WO 2006/050117 A2 | 5/2006 |
| WO | WO 2006/064344 A2 | 6/2006 |

OTHER PUBLICATIONS

International Search Report for PCT/US2005/038943, date of mailing, Mar. 16, 2006, 3 pages.
International Search Report for PCT/US2005/038944, date of mailing, Mar. 31, 2006, 3 pages.
Peramunage et al., Preparation of Micro-Sized $Li_4Ti_5O_{12}$ and Its Electrochemistry in Polyacrylonitrile Electrolye-Based Lithium Cells, Technical Papers, Electrochemical Science and Technology, J. Electrochem Soc., vol. 145, No. 8, Aug. 1998 © The Electrochemical Society, Inc., 7 pages.
Ohzuku et al., Zero-Strain Insertion Material of $Li[Li_{1/3}Ti_{5/3}]O_4$ for Rechargeable Lithium Cells, Electrochemical Science and Technology, J. Electrochem Soc., vol. 142, No. 5, May 1995 © The Electrochemical Society, Inc., 5 pages.
International Search Report for PCT/US2005/038970, date of mailing Oct. 25, 2006, 3 pages.
International Search Report for PCT/US2005/038761, date of mailing Oct. 4, 2006, 2 pages.
International Search Report for PCT/US2005/038762, date of mailing Oct. 2, 2006, 2 pages.
Office Action for U.S. Appl. No. 10/978,722; dated Mar. 14, 2008, 9 pages.
Response to Office Action for U.S. Appl. No. 10/978,722, dated Jul. 14, 2008, and Declaration Under 37 C.F.R. § 1.131, dated Jul. 14, 2008, 28 pages.

Dahn et al., "Combinatorial Study of Snl-xCox (0<x<0.6) and [Sn0.55Co0.45]1-yCy (0<y<0.5) Alloy Negative Electrode Materials for Li-Ion Batteries," Journal of Electrochemical Society, vol. 153, 2006, pp. A361-365.
Fauteux et al., "Rechargeable lithium battery anodes: alternatives to metallic lithium," Journal of Applied Electrochemistry, vol. 23, 1993, pp. 1-10.
Guyomard et al., "New amorphous oxides as high capacity negative electrodes for lithium6 batteries the LixMVO4 (M=Ni, Co, Cd, Zn; 1 <x<8) series," Journal of Power Sources, vol. 68, 1997, pp. 692-697.
Linden, David, Editor in Chief, Handbook of Batteries, Second Edition, McGraw-Hill, NY, 1995, 6 pages.
Ohzuku et al., "Why transition metal (di)oxides are the most attractive materials for batteries," Solid State Ionics, vol. 69, 1994, pp. 201-211.
Poizot et al., "Nano-sized transition-metal oxides as negative-electrode materials for lithium-ion batteries," Nature, vol. 407, 2000, cover and pp. 496-499.
Trifonova et al., "Sn-Sb and Sn-Bi Alloys as Anode Materials for Lithium-Ion Batteries," Ionics, vol. 8, 2002, cover and pp. 321-328.
Winter et al., "Insertion Electrode Materials for Rechargeable Lithium Batteries," Advanced Materials, vol. 10, 1998, pp. 725-763.
Winter et al., "Electrochemical lithiation of tin and tin-based intermetallics and composites," Electrochimica Acta, vol. 45, 1999, pp. 31-50.
Amendment and Reply for U.S. Appl. No. 10/978,722, filed with the USPTO on Jan. 17, 2007, 12 pages.
Non-Final Office Action for U.S. Appl. No. 10/978,722, dated Mar. 29, 2007, 12 pages.
Amendment and Reply for U.S. Appl. No. 10/978,722, filed with the USPTO on Jul. 30, 2007, 15 pages.
Final Office Action for U.S. Appl. No. 10/978,722, dated Oct. 9, 2007, 6 pages.
Request for Continued Examination (RCE), Reply and Interview Summary and Declaration Under 37 Cfr 1.131, filed with the USPTO on Jan. 9, 2008, 28 pages.
Non-Final Office Action for U.S. Appl. No. 10/978,722, dated Sep. 5, 2008, 14 pages.
Amendment and Reply and Terminal Disclaimer for U.S. Appl. No. 10/978,722, filed Dec. 5, 2008, 29 pages.
U.S. Appl. No. 12/112,979, filed Apr. 30, 2008, Scott et al.
International Search Report and Written Opinion for Application No. PCT/US2008/066809, mailing date Oct. 29, 2008, 8 pages.
International Search Report and Written Opinion for Application No. PCT/US2008/066801, mailing date Oct. 29, 2008, 10 pages.
International Search Report and Written Opinion for Application No. PCT/US2008/066803, date of mailing Oct. 7, 2008, 12 pages.
International Search Report and Written Opinion for Application No. PCT/US2008/082598, date of mailing Feb. 18, 2009, 11 pages.
Final Office Action for U.S. Appl. No. 10/978,722, dated Mar. 4, 2009, 10 pages.
Cava et al., The Crystal Structures of the Lithium-Inserted Metal Oxides $Li_{0.5}TiO_2$ Anatase, $LiTi_2O_4$ Spinel, and $Li_2Ti_2O_4$, Journal of Solid State Chemistry, vol. 53, Jan. 1984 © Academic Press, Inc., pp. 64-75.
Murphy et al., Lithium Insertion in Anatase: A New Route to the Spinel $LiTi_2O_4$, Revue De Chimie Minerale, vol. 19, 1982, 9 pages.
Mikula et al., Photoelectrochernical Properties of Anodic $TiO_2$ Layers Prepared by Various Current Densities, J. Electrochemical Society, vol. 139, No. 12, Dec. 1992 © The Electrochemical Society, Inc., pp. 3470-3474.
Murphy et al., Ternary $Li_xTiO_2$ Phases from Insertion Reactions, Solid State Ionics, vols. 9 & 10, 1983 © North-Holland Publishing Company, pp. 413-418.
Sasaki et al., Layered Hydrous Titanium Dioxide: Potassium Ion Exchange and Structural Characterization, Inorganic Chemistry, vol. 24, No. 14, © 1985 American Chemical Society, pp. 2265-2271.
Colbow et al., Structure and Electrochemistry of the Spinel Oxides $LiTi_2O_4$ and $Li_{4/3}Ti_{5/3}O_4$, Journal of Power Sources, vol. 26, 1989, © Elsevier Sequoia, pp. 397-402.
Brohan et al., Properties Physiques Des Bronzes $M_xTiO_2(B)$, Solid State Ionics, vols. 9 and 10, 1983, © North Holland Publishing Company, pp. 419-424.

Murphy et al., "Topochemical Reactions of Rutile Related Structures with Lithium", Mat. Res. Bull, vol. 13, No. 12, 1978, © Pergamon Press, Inc., pp. 1395-1402.

Wang et al., Li Insertion and Ion Exchange Reactions in the Ionic Conducting TI2(M,Ti)8O16 Phases with Hollandite-Type Structure, Technical Papers, Solid-State Science and Technology, J. Electrochem Soc., vol. 138, No. 1, Jan. 1991, © The Electrochemical Society, Inc.

Sawai, et al., Factors Affecting Rate Capability of a Lithium-ion Battery with $Li[Li_{1/3}Ti_{5/3}]O_4$ and $L1Co_{1/2}Ni_{1/2}O_2$, Abs. 75, 205th Meeting 1 page.

Kavan, et al., Proof of Concept—$Li_4Ti_5O_{12}$, Electrochemical and Solid State Letters, 2002, vol. 5, A39-A42, p. 13.

Wang et al., Novel Eletrolytes for Nanocrystalline $Li_4Ti_5O_{12}$ Based High Power Lithium Ion Batteries.

Ohzuku, Extended Abstracts from the Seventh Int'l Meeting on Li Batteries, Boston, MA, May 15-20, 1994, pp. 111-112.

Ohzuku, et al, "Zero-Strain Insertion Material of $Li[Li_{1/3}Ti_{5/3}]O_4$ for Rechargeable Lithium Cells", J. Electrochem. Soc. Vol. 142 #5, 1995, pp. 1431-1435.

Ferg et al, "Spinel Anodes for Lithium-Ion Batteries", J. Electrochem. Soc. vol. 141 #11, 1994, pp. L147- L150.

Zaghib, et al, "Electrochemical Study of $Li_4Ti_5O_{12}$ As Negative Electrode for Li-Ion Polymer Rechargeable Batteries", Journal of Power Sources, 81-82, 1999, pp. 300-305.

Jansen, et. al., "Development of A High-Power Lithium-Ion Battery", Journal of Power Sources, 81-82, 1999, pp. 902-905.

Ariyoshi, et. al., "Three-Volt Lithium-Ion Battery with $Li[Ni_{1/2}Mn_{3/2}]O_4$ and the Zero-Strain Insertion Material of $Li[Li_{1/3}Ti_{5/3}]O_4$", Journal of Power Sources, 119-121, 2003, pp. 959-963.

Singhal, et al. "Nanostructured Electrodes for Next Generation Rechargeable Electrochemical Devices", Journal of Power Sources, 129, 2004, pp. 38-44.

FMC Lithium, CAS No. 74389-93-2, "Stabilized Lithium Metal Powder" Product Specification, Copyright 2001 FMC Corporation (2 pages).

Jarvis et al., "A Li-Ion Cell Containing a Non-Lithiated Cathode", Abs. 182, IMLB 12 Meeting (1 page).

Ohzuku et al., "Lithium-Ion Batteries of $Li[Li_{1/3}Ti_{5/3}]O_4$ With Selected Postive-Electrode Materials for Long-Life Power Application", Abs. 23, IMLB 12 Meeting (1 page).

New $Li_4Ti_5O_{12}$ Anode Material of Süd-Chemie AG for Lithium Ion Batteries, Süd-Chemie EXM 1037—$Li_4Ti_5O_{12}$. Product Specification (2 pages).

"Battery Materials—Ceramic Anode Material for 2.4 V Lithium-Ion Batteries"—EXM 1037—$Li_4Ti_5O_{12}$ (1 page), available at least by Oct. 25, 2004.

Guerfi, et. al., "Nano Electronically Conductive Titanium-Spinel as Lithium Ion Storage Negative Electrode", Journal of Power Sources, 126, 2004, pp. 163-168.

Prosini, et. al., "$Li_4Ti_5O_{12}$ As Anode in All-Solid-State, Plastic, Lithium-Ion Batteries for Low-Power Applications" Solid State Ionics, 144, 2001, pp. 185-192.

Scrosati, "Low Voltage Lithium-Ion Cells", Advances in Lithium-Ion Batteries Kluwer Academic/Plenum Publishers, pp. 289-308.

Nakahara, et al. "Preparation of Particulate $Li_4Ti_5O_{12}$ Having Excellent Characteristics As An Electrode Active Material For Power Storage Cells", Journal of Power Sources, 117, 2003, pp. 131-136.

Medtronic Neurostimulation Systems Product Brochure, Copyright 2002 Medtronic, Inc. (6 pages).

Medtronic Activa® Product Family and Procedure Solution Product Specifications, Copyright 2003 Medtronic, Inc. (6 pages).

Request for Continued Examination (RCE), Amendment and Reply and Declaration Under 37 C.F.R. § 1.131 for U.S. Appl. No. 10/978,722, filed with the USPTO Jun. 4, 2009, 29 pages.

Notice of Allowance for U.S. Appl. No. 10/978,722, dated Jul. 9, 2009, 8 pages.

Amendment Under 37 C.F.R. § 1.312, Request for Reconsideration of Patent Term Adjustment, and Interview Summary and Express Request for Consideration of Prior Art for U.S. Appl. No. 10/978,722, filed on Aug. 7, 2009, 20 pages.

* cited by examiner

MEDICAL DEVICE HAVING LITHIUM-ION BATTERY

BACKGROUND

The present invention relates generally to the field of lithium batteries. Specifically, the present invention relates to lithium-ion batteries that are relatively tolerant to over-discharge conditions and medical devices which utilize such batteries.

Lithium-ion batteries include a positive current collector (e.g., aluminum such as an aluminum foil) having an active material provided thereon (e.g., $LiCoO_2$) and a negative current collector (e.g., copper such as a copper foil) having an active material (e.g., a carbonaceous material such as graphite) provided thereon. Together the positive current collector and the active material provided thereon are referred to as a positive electrode, while the negative current collector and the active material provided thereon are referred to as a negative electrode.

FIG. 1 shows a schematic representation of a portion of a lithium-ion battery 10 such as that described above. The battery 10 includes a positive electrode 20 that includes a positive current collector 22 and a positive active material 24, a negative electrode 30 that includes a negative current collector 32 and a negative active material 34, an electrolyte material 40, and a separator (e.g., a polymeric microporous separator, not shown) provided intermediate or between the positive electrode 20 and the negative electrode 30. The electrodes 20, 30 may be provided as relatively flat or planar plates or may be wrapped or wound in a spiral or other configuration (e.g., an oval configuration). The electrode may also be provided in a folded configuration.

During charging and discharging of the battery 10, lithium ions move between the positive electrode 20 and the negative electrode 30. For example, when the battery 10 is discharged, lithium ions flow from the negative electrode 30 to the to the positive electrode 20. In contrast, when the battery 10 is charged, lithium ions flow from the positive electrode 20 to the negative electrode 30.

FIG. 2 is a graph 100 illustrating the theoretical charging and discharging behavior for a conventional lithium-ion battery. Curve 110 represents the electrode potential versus a lithium reference electrode for a positive electrode that includes an aluminum current collector having a $LiCoO_2$ active material provided thereon, while curve 120 represents the electrode potential versus a lithium reference electrode for a negative electrode that includes a copper current collector having a carbonaceous active material provided thereon. The difference between curves 110 and 120 is representative of the overall cell voltage.

As shown in FIG. 2, upon initial charging to full capacity, the potential of the positive electrode, as shown by curve 110, increases from approximately 3.0 volts to a point above the corrosion potential of copper used to form the negative electrode (designated by dashed line 122). The potential of the negative electrode decreases from approximately 3.0 volts to a point below the decomposition potential of the $LiCoO_2$ active material provided on the aluminum current collector (designated by dashed line 112). Upon initial charging, the battery experiences an irreversible loss of capacity due to the formation of a passive layer on the negative current collector, which may be referred to as a solid-electrolyte interface ("SEI"). The irreversible loss of capacity is shown as a ledge or shelf 124 in curve 120.

One difficulty with conventional lithium-ion batteries is that when such a battery is discharged to a point near zero volts, it may exhibit a loss of deliverable capacity and corrosion of the negative electrode current collector (copper) and possibly of the battery case, depending on the material used and the polarity of the case. As shown in FIG. 2, after initial charging of the battery, a subsequent discharge of the battery in which the voltage of the battery approaches zero volts (i.e., zero percent capacity) results in a negative electrode potential that follows a path designated by dashed line 126. As shown in FIG. 2, the negative electrode potential levels off or plateaus at the copper corrosion potential of the negative current collector (approximately 3.5 volts for copper and designated by dashed line 122 in FIG. 2).

The point at which the curves 110 and 120 cross is sometimes referred to as the zero voltage crossing potential, and corresponds to a cell voltage that is equal to zero (i.e., the difference between the two curves equals zero at this point). Because of the degradation of the copper current collector which occurs at the copper corrosion potential, the copper material used for the negative current collector corrodes before the cell reaches a zero voltage condition, resulting in a battery that exhibits a dramatic loss of deliverable capacity.

While FIG. 2 shows the theoretical charging and discharging behavior of a battery that may experience corrosion of the negative current collector when the battery approaches a zero voltage configuration, it should be noted that there may also be cases in which the active material on the positive current collector may degrade in near-zero-voltage conditions. In such cases, the theoretical potential of the positive electrode versus a lithium reference electrode would decrease to the decomposition potential of the positive active material (shown as line 112 in FIG. 2), at which point the positive active material would decompose, resulting in potentially decreased protection against future over-discharge conditions.

Because damage to the lithium-ion battery may occur in the event of a low voltage condition, conventional lithium-ion batteries may include protection circuitry and/or may be utilized in devices that include protection circuitry which substantially reduces the current drain from the battery (e.g., by disconnecting the battery).

The medical device industry produces a wide variety of electronic and mechanical devices for treating patient medical conditions. Depending upon the medical condition, medical devices can be surgically implanted or connected externally to the patient receiving treatment. Clinicians use medical devices alone or in combination with drug therapies and surgery to treat patient medical conditions. For some medical conditions, medical devices provide the best, and sometimes the only, therapy to restore an individual to a more healthful condition and a fuller life.

It may be desirable to provide a source of battery power for such medical devices, including implantable medical devices. In such cases, it may be advantageous to provide a battery that may be recharged. It may also be advantageous to provide a battery that may be discharged to a near zero voltage condition without substantial risk that the battery may be damaged (e.g., without corroding one of the electrodes or the battery case, decomposing the positive active material, etc.) such that the performance of the battery is degraded in subsequent charging and discharging operations.

It would be advantageous to provide a battery (e.g., a lithium-ion battery) that may be discharged to near zero volts without producing a subsequent decrease in the amount of deliverable capacity or producing a corroded negative electrode or battery case. It would also be advantageous to provide a battery that compensates for the irreversible loss of capacity resulting from initial charging of the battery to allow the battery to be used in near zero voltage conditions without significant degradation to battery performance. It would also be advantageous to provide a medical device (e.g., an implantable medical device) that utilizes a battery that includes any one or more of these or other advantageous features.

SUMMARY

An exemplary embodiment relates to a medical device that includes a rechargeable lithium-ion battery for providing power to the medical device. The lithium-ion battery includes a positive electrode including a current collector and a first active material, a negative electrode including a current collector and a second active material, and an auxiliary electrode including a current collector and a third active material. The auxiliary electrode is configured for selective electrical connection to one of the positive electrode and the negative electrode. The first active material, second active material, and third active material are configured to allow doping and undoping of lithium ions. The third active material exhibits charging and discharging capacity below a corrosion potential of the current collector of the negative electrode and above a decomposition potential of the first active material.

Another exemplary embodiment relates to a device for providing a therapeutic treatment to a patient. The device includes a rechargeable battery for providing power for the device. The battery includes a first electrode including a first current collector and a first active material provided on the first current collector; a second electrode including a second current collector and a second active material provided on the second current collector; and a third electrode including a third current collector and a third active material provided on the third current collector. The third electrode is configured for selective electrical coupling to and decoupling from the second electrode.

Another exemplary embodiment relates to a system for providing a medical treatment to a patient. The system includes a lithium-ion battery configured to provide power to the system and capable of being charged and discharged. The lithium-ion battery includes a positive electrode having a positive current collector and an active material provided on at least one side of the positive current collector. The lithium-ion battery also includes a negative electrode having a negative current collector and a primary active material provided on at least one side of the negative current collector. The lithium-ion battery also includes an auxiliary electrode having a current collector and an auxiliary active material provided on at least one side of the current collector of the auxiliary electrode. The auxiliary electrode configured to be selectively coupled to the negative electrode when a predetermined condition is present.

Another exemplary embodiment relates to a method of treating a medical condition of a patient that includes providing at least a portion of a medical device in contact with the patient and providing a treatment to the patient utilizing the medical device. The medical device receives power from a battery that includes a positive electrode having a current collector and a first active material, a negative electrode having a current collector and a second active material, and an auxiliary electrode having a current collector and a third active material. The auxiliary electrode is configured for selective electrical connection to one of the positive electrode and the negative electrode. The first active material, second active material, and third active material are configured to allow doping and undoping of lithium ions, and the third active material exhibits charging and discharging capacity below a corrosion potential of the current collector of the negative electrode and above a decomposition potential of the first active material.

DETAILED DESCRIPTION OF THE EXEMPLARY EMBODIMENTS

Figure 3:
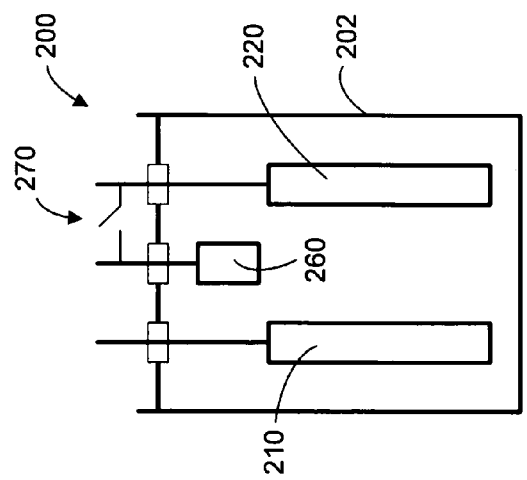
FIG. 3 is a schematic view of a portion of a lithium-ion battery having an auxiliary negative electrode according to an exemplary embodiment.

With reference to FIG. 3, a schematic view of a portion of a lithium-ion battery 200 having a case 202 is shown according to an exemplary embodiment. According to an exemplary embodiment, the battery 200 has a rating of between approximately 10 and 1000 milliampere hours (mAh). According to another exemplary embodiment, the battery has a rating of between approximately 100 and 400 mAh. According to another exemplary embodiment, the battery is an approximately 300 mAh battery. According to another exemplary embodiment, the battery is an approximately 75 mAh battery.

The battery 200 includes at least one positive electrode 210, at least one negative electrode 220, and an auxiliary electrode 260 that may be selectively electrically connected or coupled to the negative electrode 220 (e.g., by a switch 270, and according to another exemplary embodiment, according to a diode or other device). The auxiliary electrode 260, while being shown in the headspace of the battery 200, may be provided in other locations as may be desired. Also, it should be noted that one of the positive electrode 210 and negative electrode 220 may be coupled to the case 202 (e.g., as opposed to being electrically isolated from the case) according to other exemplary embodiments. The electrodes may be provided as flat or planar components of the battery 200, may be wound in a spiral or other configuration, or may be provided in a folded configuration. For example, the electrodes may be wrapped around a relatively rectangular mandrel such that they form an oval wound coil for insertion into a relatively prismatic battery case. According to other exemplary embodiments, the battery may be provided as a button cell battery, a thin film solid state battery, or as another lithium-ion battery configuration.

The battery case may be made of stainless steel or another metal. According to an exemplary embodiment, the battery case may be made of titanium, aluminum, or alloys thereof. According to another exemplary embodiment, the battery case may be made of a plastic material or a plastic-foil laminate material (e.g., an aluminum foil provided intermediate a polyolefin layer and a polyester layer).

According to an exemplary embodiment, the negative electrode is coupled to a stainless steel case by a member or tab comprising nickel or a nickel alloy. An aluminum or aluminum alloy member or tab may be coupled or attached to the positive electrode. The nickel and aluminum tabs may serve as terminals for the battery according to an exemplary embodiment.

The dimensions of the battery 200 may differ according to a variety of exemplary embodiments. For example, according to one exemplary embodiment in which the electrodes are wound such that they may be provided in a relatively prismatic battery case, the battery has dimensions of between approximately 30-40 mm by between approximately 20-30 mm by between approximately 5-7 mm. According to another exemplary embodiment, the dimensions of the battery are approximately 20 mm by 20 mm by 3 mm. According to another exemplary embodiment, a battery may be provided in the form of a button cell type battery having a diameter of approximately 30 mm and a thickness of approximately 3 mm. It will be appreciated by those of skill in the art that such dimensions and configurations as are described herein are illustrative only, and that batteries in a wide variety of sizes, shapes, and configurations may be produced in accordance with the novel concepts described herein.

According to an exemplary embodiment, the negative electrode 220 and the auxiliary electrode 260 are provided within the battery such that they are electrically isolated from one another. For example, an insulative material (e.g., a porous polymeric material (e.g., polypropylene, polyethylene, etc.), a glass, or a ceramic material) may be provided between the negative electrode 220 and the auxiliary electrode 260.

Figure 1:
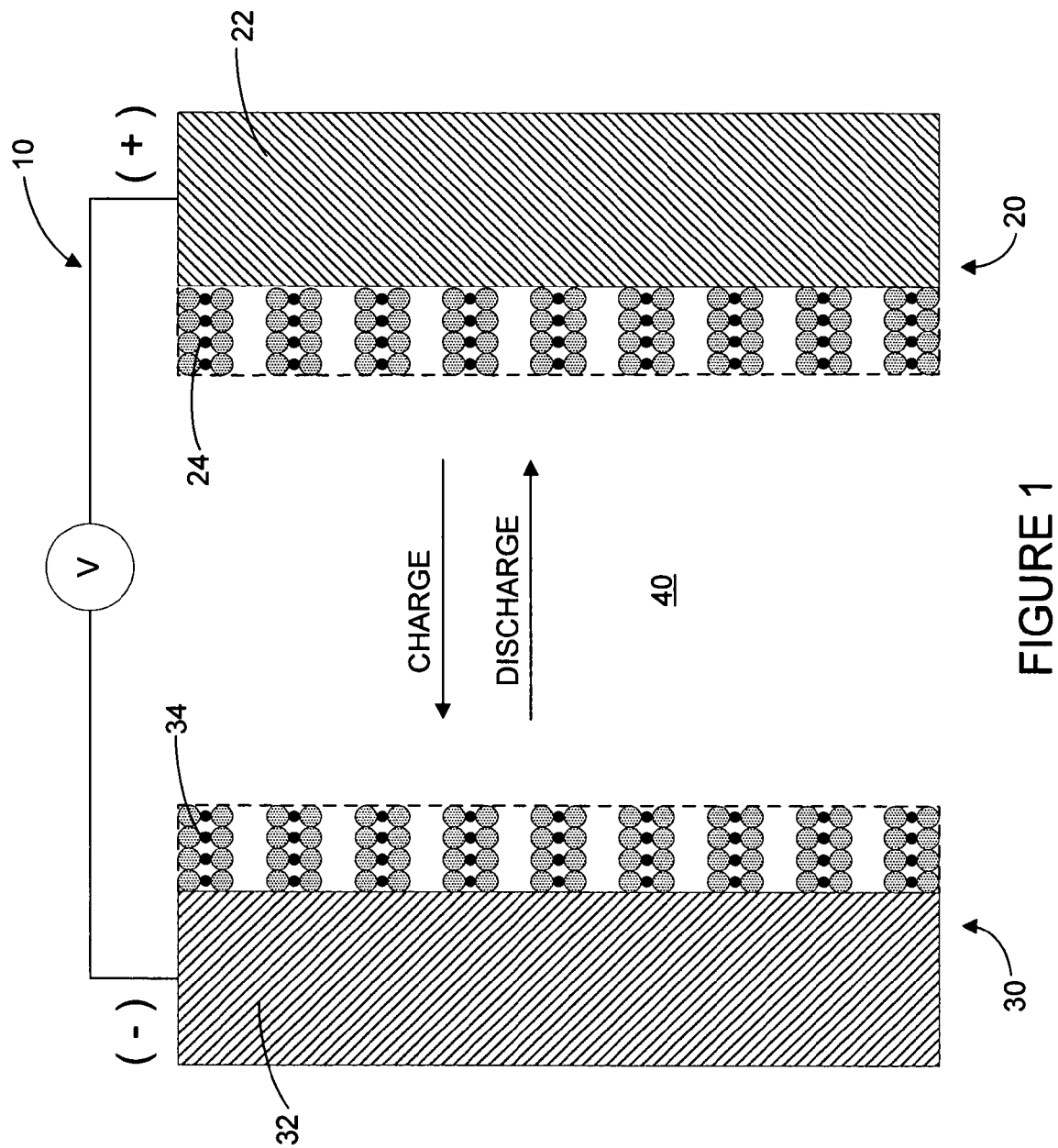
FIG. 1 is a schematic cross-sectional view of a conventional lithium-ion battery.
Figure 2:
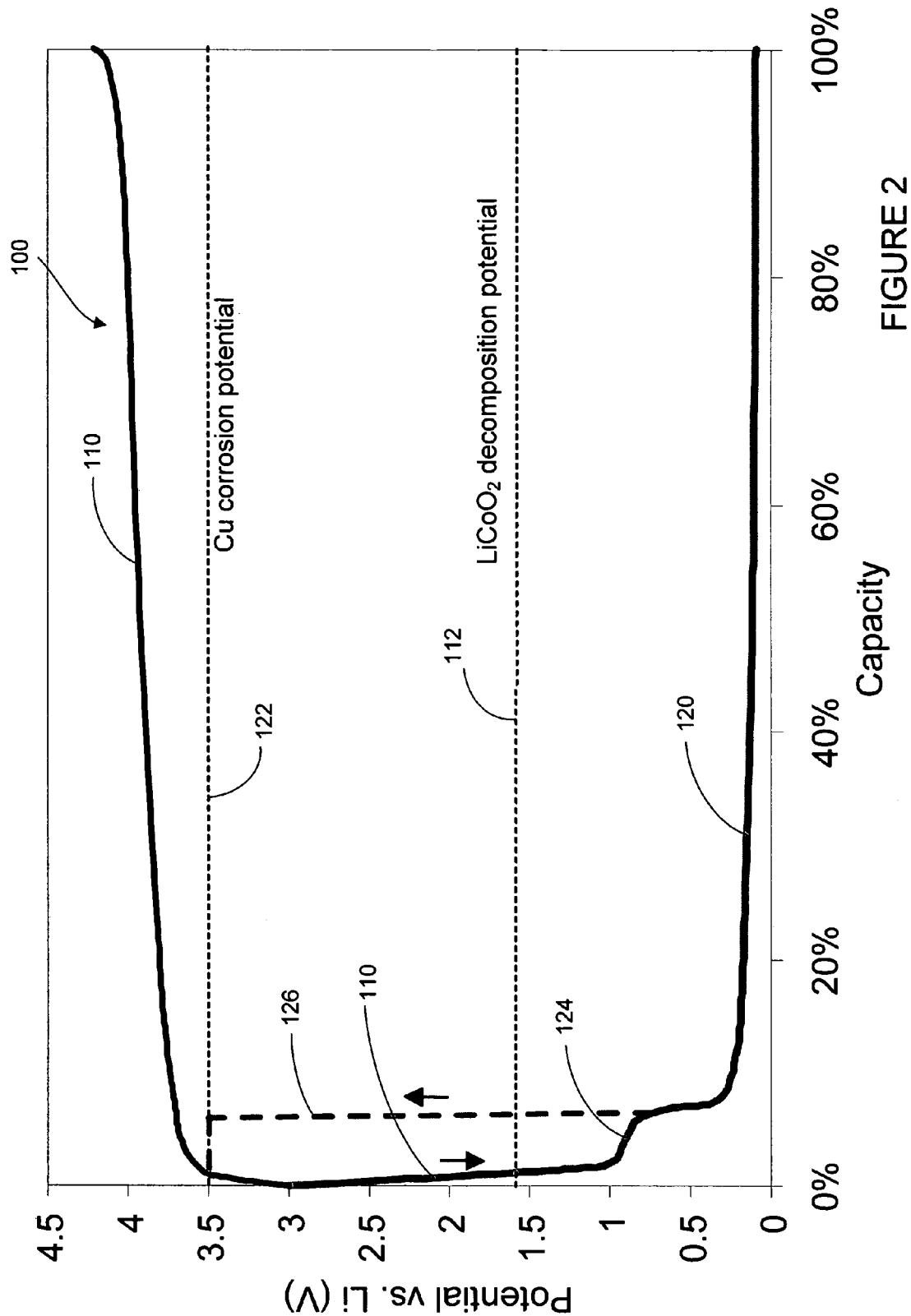
FIG. 2 is a graph illustrating the theoretical charging and discharging behavior for a conventional lithium-ion battery such as that shown schematically in FIG. 1.
Figure 4:
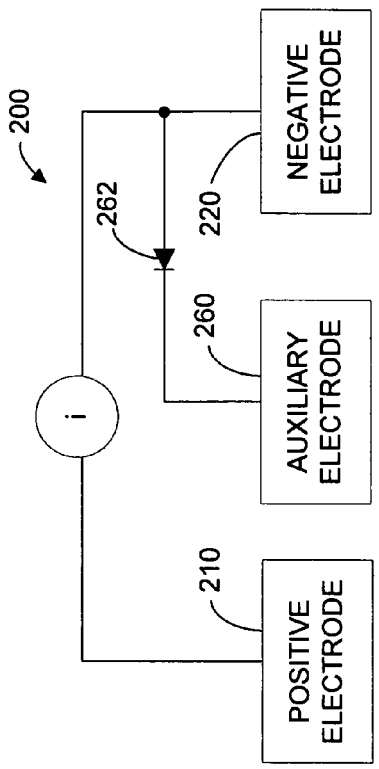
FIG. 4 is a schematic view of the lithium-ion battery shown in FIG. 3 according to one exemplary embodiment.

The auxiliary electrode 260 may be selectively electrically connected or coupled to the negative electrode 220 by way of a connection provided external to the battery. The selective electrical connection and disconnection between the auxiliary electrode 260 and the negative electrode 220 may be accomplished in any of a variety of ways. For example, FIG. 4 illustrates a configuration in which the auxiliary electrode 260 and negative electrode 220 are connected by way of a diode 262 (or a plurality of diodes according to another embodiment) placed between the auxiliary electrode 260 and the negative electrode 220. According to this exemplary embodiment, the diode or series of diodes may be configured such that an electrical connection between the auxiliary electrode 260 and negative electrode 220 occurs only when the potential difference between the negative electrode 220 and the auxiliary electrode 260 exceeds a predetermined threshold value (e.g., approximately 0.3 volts according to an exemplary embodiment and between approximately 0.1 and 0.5 volts according to another exemplary embodiment). The auxiliary electrode 260 and the negative electrode 220 may be disconnected (i.e., electrically isolated) whenever the potential difference between the negative electrode and the auxiliary electrode falls below the predetermined value. According to an exemplary embodiment, the diode 262 is a 0.3 volt diode. According to other exemplary embodiments, the diode 262 or series of diodes have a voltage of between approximately 0.2 and 0.7 volts. According to an exemplary embodiment, the potential difference at which the connection and disconnection of the auxiliary electrode 260 and the negative electrode 220 occurs is selected such that the potential of the auxiliary electrode material always remains above its reductive decomposition potential.

Figure 5:
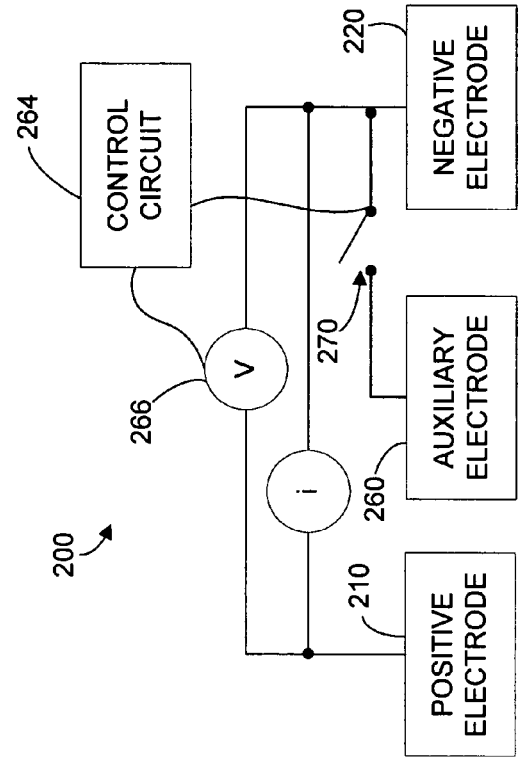
FIG. 5 is a schematic view of the lithium-ion battery shown in FIG. 3 according to another exemplary embodiment.

FIG. 5 illustrates a configuration for the battery 200 according to another exemplary embodiment. A control circuit 264 (which may be implemented in hardware, software, or firmware, for example) receives input signals from a voltmeter 266 which measures the voltage between the positive electrode 210 and the negative electrode 220. When the voltage difference between the positive electrode 210 and the negative electrode 220 falls below a predetermined threshold (e.g., 1.8 volts), the control circuit instructs a switch 270 to close, thereby electrically connecting the auxiliary electrode 260 to the negative electrode 220. The switch 270 may be instructed to open (thus electrically disconnecting the negative electrode 220 and the auxiliary electrode 260) when the voltage difference between the positive electrode 210 and the negative electrode 220 exceeds the predetermined threshold.

While FIGS. 4 and 5 illustrate two embodiments in which the auxiliary electrode 260 would be electrically connected to the negative electrode 220, it should be understood by those of skill in the art that any of a variety of other mechanisms may be utilized in order to electrically connect the auxiliary electrode to the negative electrode when a predetermined condition has been satisfied. As such, the embodiment shown in FIGS. 4 and 5 should not be understood to be limiting to the scope of the invention as described in the appended claims.

Figure 6:
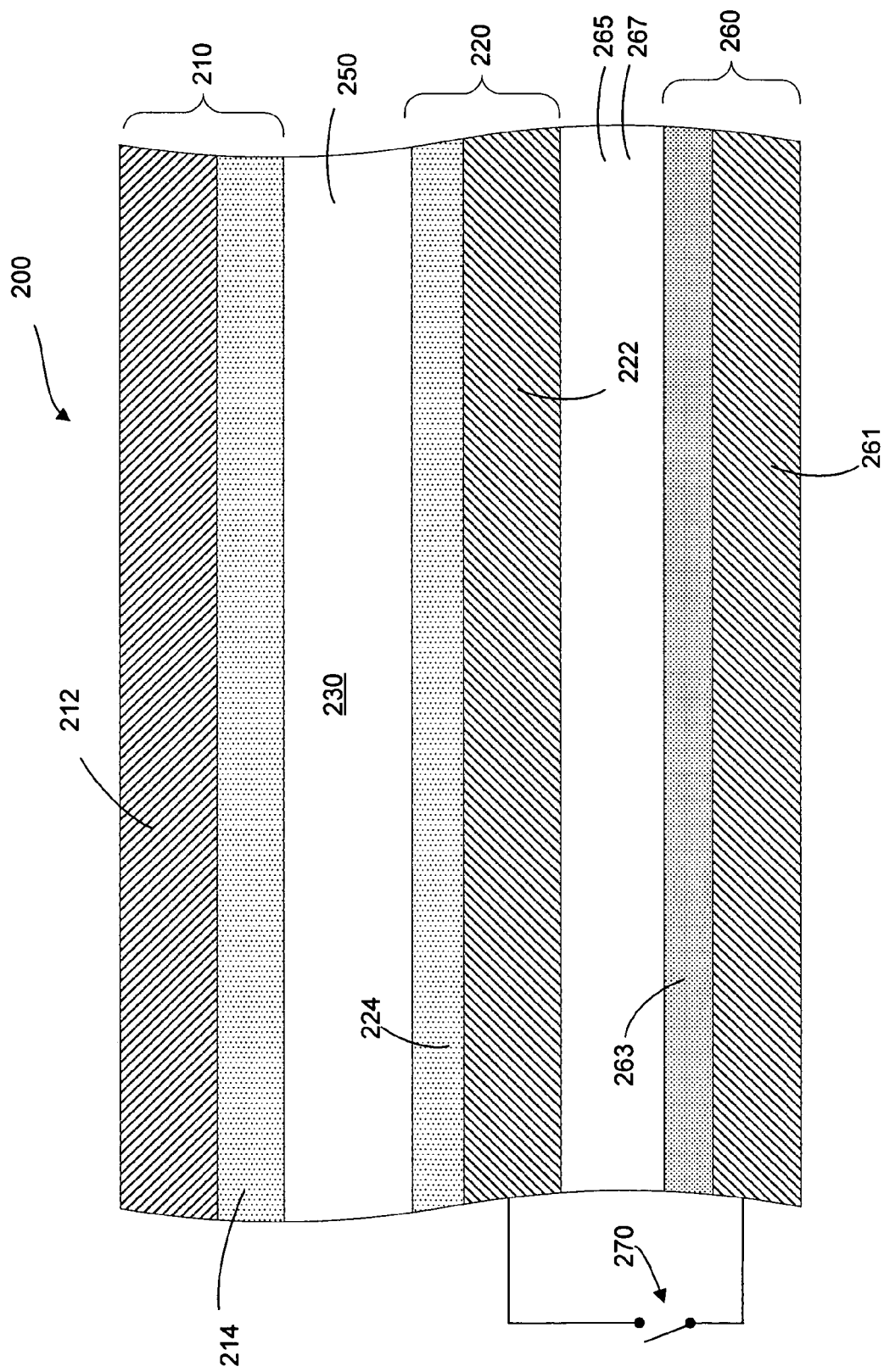
FIG. 6 is a schematic cross-sectional view of a portion of the lithium-ion battery shown in FIG. 3 according to one exemplary embodiment.

FIG. 6 is a schematic cross-sectional view of a portion of the battery 200 shown in FIG. 3. The battery 200 includes a positive electrode 210, a negative electrode 220, and an auxiliary electrode 260. The auxiliary electrode 260 may be selectively electrically coupled or connected to the negative electrode 220 by virtue of a switch 270 or other means. It should be understood that switch 270 may be a mechanism such as, but not limited to, those devices such as in the embodiments shown in FIGS. 4 and 5.

An electrolyte 230 is provided intermediate or between the positive and negative electrodes to provide a medium through which lithium ions may travel. According to an exemplary embodiment, the electrolyte may be a liquid (e.g., a lithium salt dissolved in one or more non-aqueous solvents). According to another exemplary embodiment, the electrolyte may be a lithium salt dissolved in a polymeric material such as poly (ethylene oxide) or silicone. According to another exemplary embodiment, the electrolyte may be an ionic liquid such as N-methyl-N-alkylpyrrolidinium bis(trifluoromethanesulfonyl)imide salts. According to another exemplary embodiment, the electrolyte may be a solid state electrolyte such as a lithium-ion conducting glass such as lithium phosphorous oxynitride (LiPON).

Various other electrolytes may be used according to other exemplary embodiments. For example, according to an exemplary embodiment, the electrolyte may be a 1:1 mixture of ethylene carbonate to diethylene carbonate (EC:DEC) in a 1.0 M salt of LiPF$_6$. According to another exemplary embodiment, the electrolyte may include a polypropylene carbonate solvent and a lithium bis-oxalatoborate salt (sometimes referred to as LiBOB). According to other exemplary embodiments, the electrolyte may comprise one or more of a PVDF copolymer, a PVDF-polyimide material, and organosilicon polymer, a thermal polymerization gel, a radiation cured acrylate, a particulate with polymer gel, an inorganic gel polymer electrolyte, an inorganic gel-polymer electrolyte, a PVDF gel, polyethylene oxide (PEO), a glass ceramic electrolyte, phosphate glasses, lithium conducting glasses, lithium conducting ceramics, and an inorganic ionic liquid gel, among others.

A separator 250 is provided intermediate or between the positive electrode 210 and the negative electrode 220. According to an exemplary embodiment, the separator 250 is a polymeric material such as a polypropylene/polyethelene or another polyolefin multilayer laminate that includes micropores formed therein to allow electrolyte and lithium ions to flow from one side of the separator to the other. The thickness of the separator 250 is between approximately 10 micrometers (μm) and 50 μm according to an exemplary embodiment. According to a particular exemplary embodiment, the thickness of the separator is approximately 25 μm and the average pore size of the separator is between approximately 0.02 μm and 0.1 μm.

The auxiliary electrode 260 is electrically isolated from the negative electrode 220 internal to the battery, and is electrically connected to the negative electrode 220 only by virtue of the external connection means (shown, e.g., as switch 270). An insulative material 265 such as a porous polypropylene or polyethylene separator, a glass (e.g., Cabal-12 glass), or a ceramic material (e.g., alumina) may be provided intermediates or between the negative electrode 220 and the auxiliary electrode 260 according to exemplary embodiment (an electrolyte 267 similar to that described above as electrolyte 230 may also be provided intermediate or between the auxiliary electrode 260 and the negative electrode 220).

The positive electrode 210 includes a current collector 212 made of a conductive material such as a metal. According to an exemplary embodiment, the current collector 212 comprises aluminum or an aluminum alloy. According to an exemplary embodiment, the thickness of the current collector 212 is between approximately 5 μm and 75 μm. According to a particular exemplary embodiment, the thickness of the current collector 212 is approximately 20 μm. It should also be noted that while the positive current collector 212 has been illustrated and described as being a thin foil material, the positive current collector may have any of a variety of other configurations according to various exemplary embodiments. For example, the positive current collector may be a grid such as a mesh grid, an expanded metal grid, a photochemically etched grid, or the like.

The current collector 212 has a layer of active material 214 provided thereon (e.g., coated on the current collector). While FIG. 3 shows that the active material 214 is provided on only one side of the current collector 212, it should be understood that a layer of active material similar or identical to that shown as active material 214 may be provided or coated on both sides of the current collector 212.

According to an exemplary embodiment, the active material 214 is a material or compound that includes lithium. The lithium included in the active material 214 may be doped and undoped during discharging and charging of the battery, respectively. According to an exemplary embodiment, the active material 214 is lithium cobalt oxide (LiCoO$_2$). According to another exemplary embodiment, the positive active material is of the form LiCo$_x$Ni$_{(1-x)}$O$_2$, with x being between approximately 0.05 and 0.8. According to another exemplary embodiment, the primary active material is of the form LiM$_x$Co$_y$Ni$_{(1-x-y)}$O$_2$, where M is aluminum or titanium, x is between approximately 0.05 and 0.3 and y is between approximately 0.1 and 0.3. According to another exemplary embodiment, the positive active material is LiCo$_x$Mn$_y$Ni$_z$O$_2$ or LiNi$_x$Co$_y$Al$_z$O$_2$. According to other exemplary embodiments, the primary active material may include LiMn$_2$O$_4$.

According to various other exemplary embodiments, the primary active material may include a material such as a material of the form Li$_{1-x}$MO$_2$ where M is a metal (e.g., LiCoO$_2$, LiNiO$_2$, and LiMnO$_2$), a material of the form Li$_{1-w}$(M'$_x$M''$_y$)O$_2$ where M' and M'' are different metals (e.g., Li(Ni$_x$Mn$_y$)O$_2$, Li(Ni$_{1/2}$Mn$_{1/2}$)O$_2$, Li(Cr$_x$Mn$_{1-x}$)O$_2$, Li(Al$_x$Mn$_{1-x}$)O$_2$, Li(Co$_x$M$_{1-x}$)O$_2$, Li(Co$_x$Ni$_{1-x}$)O$_2$, and Li(Co$_x$Fe$_{1-x}$)O$_2$)), a material of the form Li$_{1-w}$(Mn$_x$Ni$_y$Co$_z$)O$_2$ (e.g., LiCo$_x$Mn$_y$Ni$_{(1-x-y)}$O$_2$, Li(Mn$_{1/2}$Ni$_{1/2}$Co$_{1/2}$)O$_2$, Li(Mn$_{1/2}$Ni$_{1/2}$Co$_{1/2-x}$Mg$_x$)O$_2$, Li(Mn$_{0.4}$Ni$_{0.4}$Co$_{0.2}$)O$_2$, and Li(Mn$_{0.1}$Ni$_{0.1}$Co$_{0.8}$)O$_2$), a material of the form Li$_{1-w}$(Mn$_x$Ni$_x$Co$_{1-2x}$)O$_2$ a material of the form Li$_{1-x}$(Mn$_x$Ni$_y$Co$_z$Al$_w$)O$_2$ a material of the form Li$_{1-w}$(Ni$_x$Co$_y$Al$_z$)O$_2$ (e.g., Li(Ni$_{0.8}$Co$_{0.15}$Al$_{0.05}$)O$_2$), a material of the form Li$_{1-w}$(Ni$_x$Co$_y$M$_z$)O$_2$ where M is a metal, a material of the form Li$_{1-w}$(Ni$_x$Mn$_y$M$_z$)O$_2$ where M is a metal, a material of the form Li(Ni$_{x-y}$Mn$_y$Cr$_{2-x}$)O$_4$, LiMn$_2$O$_4$, a material of the form LiM'M''$_2$O$_4$ where M' and M'' are different metals (e.g., LiMn$_{2-y-z}$Ni$_y$, Li$_z$O$_4$, LiMn$_{1.5}$Ni$_{0.5}$O$_4$, LiNiCuO$_4$, LiMn$_{1-x}$Al$_x$O$_4$, LiNi$_{0.5}$Ti$_{0.5}$O$_4$, and Li$_{1.05}$Al$_{0.1}$Mn$_{1.85}$O$_{4-z}$F$_z$), Li$_2$MnO$_3$, a material of the form Li$_x$V$_y$O$_z$ (e.g., LiV$_3$O$_8$, LiV$_2$O$_5$, and LiV$_6$O$_{13}$), a material of the form LiMPO$_4$ where M is a metal or LiM$_x$'M''$_{1-x}$PO$_4$ where M' and M'' are different metals (e.g., LiFePO$_4$, LiFe$_x$M$_{1-x}$PO$_4$, LiVOPO$_4$, and Li$_3$V$_2$(PO$_4$)$_3$, LIMPO$_{4x}$ where M is a metal such as iron or vanadium and x is a halogen such as fluorine, and combinations thereof.

A binder material may also be utilized in conjunction with the active material 214. For example, according to an exemplary embodiment, the active material may include a conductive additive such as carbon black and a binder such as polyvinylidine fluoride (PVDF) or an elastomeric polymer.

According to an exemplary embodiment, the thickness of the active material 214 is between approximately 0.1 μm and 3 mm. According to a particular exemplary embodiment, the thickness of the active material 214 is between approximately 25 μm and 300 μm. According to a particular exemplary embodiment, the thickness of the layer of active material 214 is approximately 75 μm.

The negative current collector 222 included as part of the negative electrode 220 is made of a conductive material such as a metal. According to an exemplary embodiment, the current collector 222 is copper or a copper alloy. According to another exemplary embodiment, the current collector 222 is titanium or a titanium alloy. According to another exemplary embodiment, the current collector 222 is nickel or a nickel alloy. According to another exemplary embodiment in which the negative active material 224 is not carbon, the current collector 222 is aluminum or an aluminum alloy. It should also be noted that while the negative current collector 222 has been illustrated and described as being a thin foil material, the positive current collector may have any of a variety of other configurations according to various exemplary embodiments. For example, the positive current collector may be a grid such as a mesh grid, an expanded metal grid, a photochemically etched grid, or the like.

According to an exemplary embodiment, the thickness of the current collector 222 is between approximately 100 nm and 100 µm. According to a particular exemplary embodiment, the thickness of the current collector 222 is between approximately 5 µm and 25 µm. According to a particular exemplary embodiment, the thickness of the current collector is approximately 10 µm.

The negative current collector 222 has a layer of active material 224 provided thereon. While FIG. 3 shows that the active material 224 is provided on only one side of the current collector 222, it should be understood that a layer of active material similar or identical to that shown may be provided or coated on both sides of the current collector 222. According to an exemplary embodiment, the active material 224 may include a conductive additive such as carbon black and a binder such as polyvinylidine fluoride (PVDF) or an elastomeric polymer.

According to an exemplary embodiment the active material 224 is a carbonaceous material (e.g., carbon such as graphite). According to another exemplary embodiment, the active material 224 is a lithium titanate material such as $Li_4Ti_5O_{12}$. One advantage of using a lithium titanate material in place of a carbonaceous material is that it is believed that the use of a lithium titanate material allows for charging and discharging of the battery at higher rates than is capable using carbonaceous materials.

Other lithium titanate materials which may be suitable for use as the active material 224 may include one or more of include the following lithium titanate spinel materials: $H_xLi_{y-x}TiO_xO_4$, $H_xLi_{y-x}TiO_xO_4$, $Li_4M_xTi_{5-x}O_{12}$, $Li_xTi_yO_4$, $Li_xTi_yO_4$, $Li_4[Ti_{1.67}Li_{0.33-y}M_y]O_4$, $Li_2TiO_3$, $Li_4Ti_{4.75}V_{0.25}O_2$, $Li_4Ti_{4.75}Fe_{0.25}O_{11.88}$, and $Li_4Ti_{4.5}Mn_{0.5}O_{12}$, and $LiM'M''XO_4$ (where M' is a transition metal, M'' is an optional three valent non-transition metal, and X is zirconium, titanium, or a combination of these two, and where M' is nickel, cobalt, iron, manganese, vanadium, copper, chromium, molybdenum, niobium, or combinations thereof). Note that such lithium titanate spinel materials may be used in any state of lithiation (e.g., $Li_{4+x}Ti_{50}O_{12}$, where $0 \leq x \leq 3$).

One advantage of using a lithium titanate material instead of a carbonaceous material is that it is believed that the use of a lithium titanate material allows for charging and discharging of the battery at higher rates than is capable using carbonaceous materials. According to other exemplary embodiments, the negative active material 224 may be carbon, $Li_xAl$, $Li_xSn$, $Li_xSi$, $Li_xSnO$, metal nanoparticle composites (e.g., including $Li_xAl$, $Li_xSn$, $Li_xSi$, or $Li_xSnO$), or carbon-coated lithium titanate. Lithium titanate materials are also believed to offer superior cycle life because they are so called "zero-strain" materials. Zero strain materials have crystal lattices which do not experience shrinkage or contraction with lithium doping/de-doping, making them free from strain-related degradation mechanisms.

Another advantageous feature of using a lithium titanate material is that it is believed that when used in a negative electrode of a lithium-ion battery, such materials will cycle lithium at a potential plateau of about 1.5V versus a lithium reference electrode. This is substantially higher than graphitic carbon, which is traditionally used in lithium ion batteries, and cycles lithium down to about 0.1V in the fully charged state. As a result, the battery using lithium titanate is believed to be less likely to result in plating of lithium (which occurs at 0V versus a lithium reference) while being charged. Lithium plating is a well-known phenomenon that can lead to loss in performance of lithium ion batteries. Being free from the risk lithium plating, cells with lithium titanate negative electrodes may also be charged at rates that exceed those with carbon negative electrodes. For example, a common upper limit for the rate of charge in lithium ion batteries is about 1 C (meaning that the battery can be fully charged from the discharged state in one hour). Conversely, it has been reported in literature that lithium titanate may be charged at rates up to 10 C (i.e., attaining full charge in 1/10 hour, or six minutes). Being able to recharge a battery more quickly substantially increases the functionality of devices that employ such a battery. A further advantage of the higher potential of the lithium titanate material is that it avoids decomposition of organic solvents (such as propylene carbonate) commonly used in lithium ion batteries. In so doing, it may reduce negative consequences such as formation of gas, cell swelling, reduction of reversible battery capacity, and buildup of resistive films which reduce battery power.

According to various exemplary embodiments, the thickness of the active material 224 is between approximately 0.1 µm and 3 mm. According to other exemplary embodiments, the thickness of the layer of active material 224 may be between approximately 25 µm and 300 µm. According to a particular exemplary embodiment, the thickness of the active material 224 is approximately 75 µm.

The auxiliary electrode 260 includes a current collector 261 that is made of a conductive material such as a metal. According to an exemplary embodiment, the current collector 261 is titanium or a titanium alloy. According to another exemplary embodiment, the current collector 261 may be aluminum or a aluminum alloy. According to other exemplary embodiments, the current collector 261 may be nickel, stainless steel, or another suitable metal material. It should also be noted that while the current collector 261 has been illustrated and described as being a thin foil material, the current collector may have any of a variety of configurations according to various exemplary embodiments. For example, the current collector may be a grid such as a mesh grid, and an expanded metal grid, a photochemically etched grid, or the like.

According to an exemplary embodiment, the thickness of the current collector 261 is between approximately 10 and 40 µm. According to another exemplary embodiment, the thickness of the current collector is between approximately 10 µm and 20 µm. According to a particular exemplary embodiment, the thickness of the current collector 261 is approximately 10 µm.

The current collector 261 has a layer of active material 263 provided thereon. While FIG. 6 shows that the active material 263 is provided on only one side of the current collector 262, it should be understood that a layer of active material similar or identical to that shown may be provided or coated on both sides of the current collector 261.

The active material 263 is a material that is selected to have relatively significant charge and discharge capacity below the corrosion potential of the material used for the negative current collector 222 provided as part of the negative electrode 220 and above the decomposition potential of the active material 214 provided on the positive current collector 212. The active material 263 is also selected to be stable over its full potential-composition range in the electrolyte. For example, according to an exemplary embodiment in which the negative current collector 222 comprises copper, for which the corrosion potential is approximately 3.5 volts, the active material 263 includes significant charge and discharge capacity below 3.5 volts.

According to an exemplary embodiment in which the auxiliary electrode 260 is to be coupled to the negative electrode 220, the active material 263 must comprise lithium or be lithiated using a source of lithium (e.g., a lithium powder or a lithium patch, etc.) in electrical contact with the auxiliary electrode. According to an exemplary embodiment in which the active material 263 includes lithium, the active material is $LiMn_2O_4$. According to various other exemplary embodiments, the active material may be selected from the following materials and combinations thereof: $V_2O_5$, $V_6O_{13}$, $LiMn_2O_4$ (spinel), $LiM_xMn_{(2-x)}O_4$ (spinel) where M is metal (including Li) and x is between approximately 0.05 and 0.4, $Li_5Ti_4O_{12}$, $Li_xVO_2$ (where x is between approximately 0 and 1), $V_3O_8$, $MoO_3$, $TiS_2$, $WO_2$, $MoO_2$, and $RuO_2$, as well as their partially or fully lithiated counterparts.

Any lithium included in the active material 263 of the auxiliary electrode 260 has significant charge/discharge capacity that lies below the corrosion potential of the negative current collector 222 and/or any battery components to which it is electrically connected (e.g., the case) and above the decomposition potential of the positive electrode active material 214. The active material 263 contains electrochemically active lithium in the as-constructed state (completed cell including electrolyte). The lithium becomes significantly undoped at a potential below the corrosion potential for the negative current collector 222. In so doing, this material lowers the final potential of the negative electrode in the discharge state, so that the zero voltage crossing potential remains below the corrosion potential of the negative current collector and the battery case. The active material 263 may be capable of accepting the lithium when the battery is recharged.

It should be noted that while a variety of materials have been described above as being useful for active material 263, a variety of additional materials may be utilized in addition to or in place of such materials. For example, the active material 263 may comprise an oxide material such as one or more of $Li_xMoO_3$ ($0<x\leq2$), $Li_xMoO_2$ ($0<x\leq1$), $Li_xMo_2O_4$ ($0<x\leq2$), $Li_xMnO_2$ ($0<x\leq1$), $Li_xMn_2O_4$ ($0<x\leq2$), $Li_xV_2O_5$ ($0<x\leq2.5$), $Li_xV_3O_8$ ($0<x\leq3.5$), $Li_xV_6O_{13}$ ($0<x\leq6$ for $Li_xVO_{2.19}$ and $0<x\leq3.6$ for $Li_xVO_{2.17}$), $Li_xVO_2$ ($0<x\leq1$), $Li_xWO_3$ ($0<x\leq1$), $Li_xWO_2$ ($0<x\leq1$), $Li_xTiO_2$ (anatase) ($0<x\leq1$), $Li_xTi_2O_4$ ($0<x\leq2$), $Li_xRuO_2$ ($0<x\leq1$), $Li_xFe_2O_3$ ($0<x\leq2$), $Li_xFe_3O_4$ ($0<x\leq2$), $Li_xCr_2O$ ($0<x\leq3$), $Li_xCr$ ($0<x\leq3.8$), and $Li_xNi_yCo_{1-y}O_2$ ($0<x\leq1$, $0.90<y\leq1.00$).

According to another exemplary embodiment, the active material 263 may comprise a sulfide material such as one or more of $Li_xV_2S_5$ ($0<x\leq4.8$), $Li_xTaS_2$ ($0<x\leq1$), $Li_xFeS$ ($0<x\leq1$), $Li_xFeS_2$ ($0<x\leq1$), $Li_xNbS_3$ ($0<x\leq2.4$), $Li_xMoS_3$ ($0<x\leq3$), $Li_xMoS_2$ ($0<x\leq1$), $Li_xTiS_2$ ($0<x\leq1$), $Li_xZrS_2$ ($0<x\leq1$), $Li_xFe_{0.25}V_{0.75}S_2$ ($0<x\leq1$), $Li_xCr_{0.75}V_{0.25}S_2$ ($0<x\leq0.65$), and $Li_xCr_{0.5}V_{0.5}S_2$ ($0<x\leq1$).

According to another exemplary embodiment, the active material 263 may comprise a selenide material such as one or more of $Li_xNbSe_3$ ($0<X\leq3$), $Li_xVSe_2$ ($0<x\leq1$), or various other materials such as, for example, $Li_xNiPS_3$ ($0<x\leq1.5$) and $Li_xFePS_3$ ($0<x\leq1.5$).

According to an exemplary embodiment in which the active material 263 does not include lithium in the as-constructed state (e.g., the active material 263 is $V_6O_{13}$), a mechanism must be provided to lithiate the active material 263. According to an exemplary embodiment, a mass or quantity of lithium (e.g., a lithium "patch") may be provided, as will be discussed in greater detail below.

Figure 7:
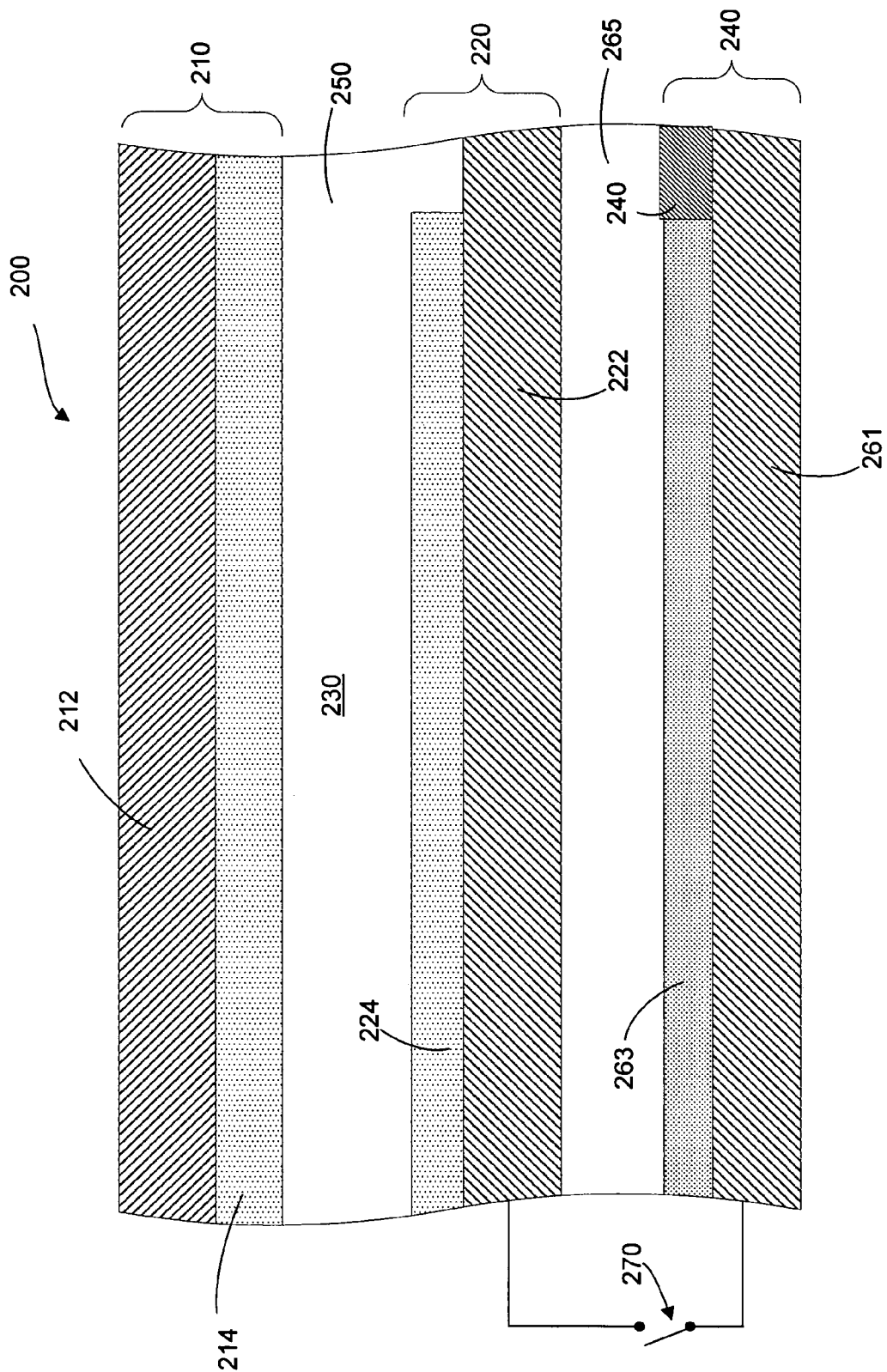
FIG. 7 is a schematic cross-sectional view of a portion of the lithium-ion battery shown in FIG. 3 according to another exemplary embodiment.

FIG. 7 shows a battery 200 according to another exemplary embodiment in which a mass or quantity of lithium 240 (e.g., a lithium patch) is provided in electrical contact with current collector 261 of the auxiliary electrode 260 to lithiate active material 263. Such a configuration corresponds to a situation in which the active material 263 is provided without including electrochemically active lithium (e.g., the active material 263 does not include lithium as it is coated on the negative current collector). One such exemplary embodiment involves the use of $V_2O_5$ for the active material 263. In contrast, FIG. 6 shows a configuration in which the active material 263 is provided as a lithiated material (e.g., $LiMn_2O_4$). In such an embodiment, a mass or quantity of lithium in contact with the current collector 261 of the auxiliary electrode 260 is not necessary.

The electrochemically active lithium may be provided in other locations in the negative electrode 220 and/or may have a different size or shape than that shown schematically in FIG. 7. For example, the electrochemically active lithium may be provided as a disc or as a rectangular piece of material coupled to the negative current collector. While the electrochemically active lithium is shown as being provided on a single side of the current collector 261 in FIG. 7 (e.g., as a lithium patch), separate lithium patches may be provided on opposite sides of the current collector 261. Further, multiple lithium patches may be provided on one or more of the sides of the current collector 261. In another example, the lithium may be provided elsewhere within the battery and connected (e.g., by a wire) to the current collector 261.

According to another exemplary embodiment, the electrochemically active or cyclable lithium may be added as finely divided or powdered lithium. Such powdered lithium includes a passive coating (e.g., a thin layer or film of lithium carbonate) provided thereon to reduce the reactivity of the powdered lithium with air and moisture. Such material may be mixed with the auxiliary electrode active material prior to application of the auxiliary electrode active material to fabrication of the cells or may be added as another separate active material layer. According to an exemplary embodiment, the finely divided or powdered lithium has a diameter of between approximately 1 μm and 100 μm, and according to a particular embodiment, between approximately 5 μm and 30 μm.

According to an exemplary embodiment in which a lithium patch 240 is utilized, the size of the lithium patch 240 is sufficient to fully lithiate the auxiliary electrode active material 263. According to an exemplary embodiment, the size of the lithium patch is between approximately 1.4 cm×1.4 cm×0.11 cm, which corresponds to approximately 0.013 grams (e.g., approximately 50 mAh). The specific size of the lithium patch may vary according to other exemplary embodiments (e.g., approximately 5% of the capacity of either the negative or positive electrode).

Figure 8:
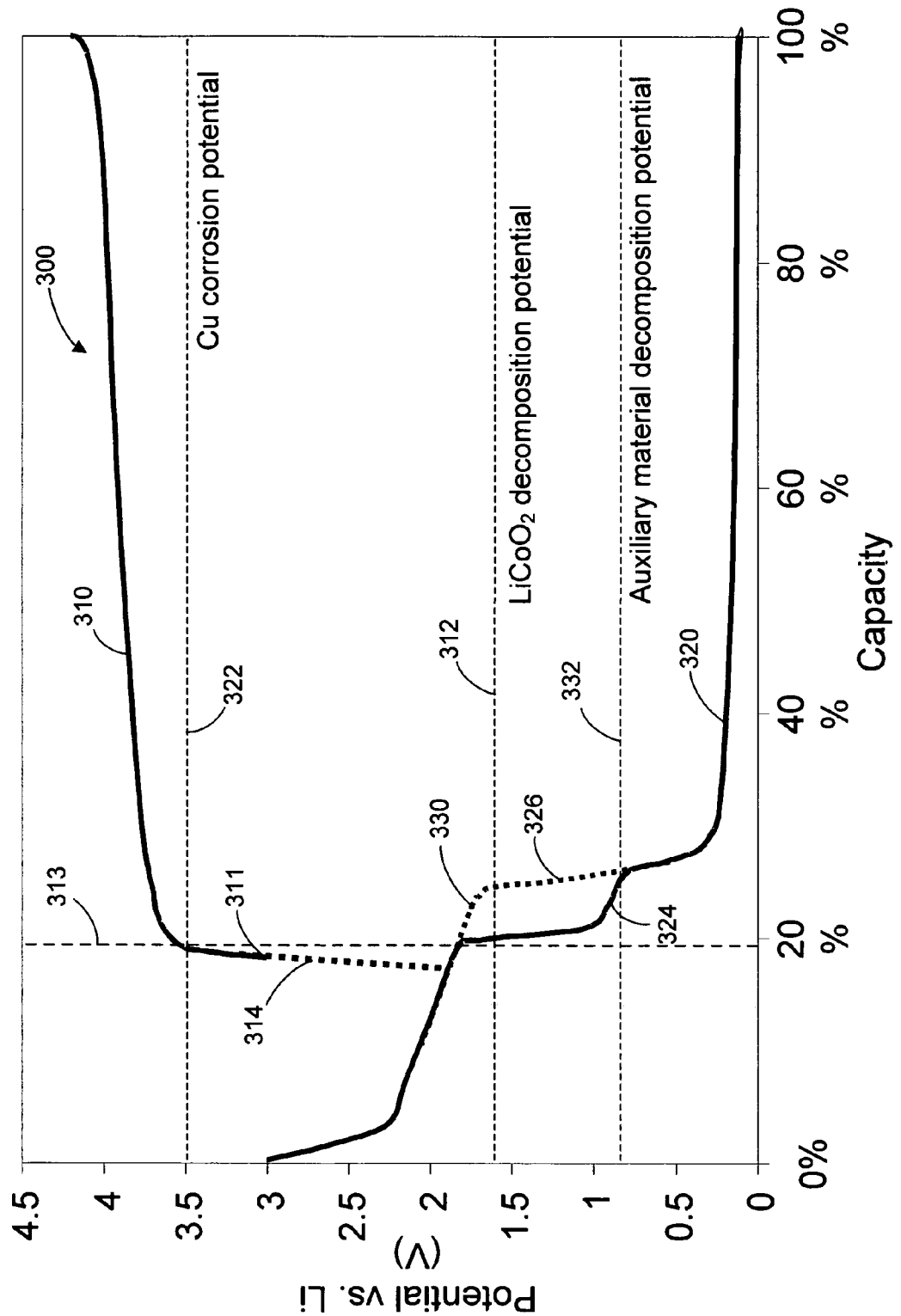
FIG. 8 is a graph illustrating the theoretical charging and discharging behavior for a lithium-ion battery such as that shown in FIG. 3.

FIG. 8 is a graph 300 illustrating the theoretical charging and discharging behavior for a lithium-ion battery constructed in accordance with an exemplary embodiment such as that shown and described with regard to FIGS. 3-7. Curve 310 represents the electrode potential versus a lithium reference electrode for a positive electrode (e.g., positive electrode 210) that includes an aluminum current collector having a $LiCoO_2$ primary active material provided thereon.

Curve 320 represents the electrode potential versus a lithium reference electrode for a negative electrode that includes a copper current collector having an active material (i.e., an active material 224 including, for example, a carbonaceous material such as carbon), a non-lithiated active material provided on an auxiliary electrode, and a lithium patch provided on the auxiliary electrode. The difference between curves 310 and 320 is representative of the overall cell voltage of the battery.

The active material provided on the auxiliary electrode is selected to provide significant charging/discharging capacity below the corrosion potential (shown as dashed line 322) of the negative current collector and above the decomposition potential (shown as dashed line 312) of the $LiCoO_2$ positive electrode active material, in addition to its ability to remain stable over its full potential-composition range in the electrolyte. According to an exemplary embodiment, the secondary active material is $V_6O_{13}$. According to various other exemplary embodiments, the secondary active material may be selected from the following materials and combinations thereof: $V_2O_5$, $V_6O_{13}$, $V_3O_8$, $MoO_3$, $TiS_2$, $WO_2$, $MoO_2$, and $RuO_2$.

It should be noted that the theoretical charging and discharge behavior for the negative electrode is believed to be qualitatively similar to that shown in FIG. 8 for a copper current collector having a $Li_4Ti_5O_{12}$ primary active material provided thereon (as opposed to a carbon active material), with the relatively flat portion of the curve 320 being shifted upward to a level of approximately 1.57 volts (in contrast to the approximately 0.1 volts for the carbon active material).

As shown in FIG. 8, when the battery is first constructed and electrolyte is provided within the battery, the potentials of the positive and negative electrodes begin at the point shown as dashed line 313. Upon initial charging to full capacity, the potential of the positive electrode, as shown by curve 310, increases from approximately 3.0 volts (shown as point 311) to a point above the corrosion potential of copper used to form the negative current collector (designated by dashed line 322). When the battery is subsequently discharged toward a zero voltage condition, the positive electrode potential will continue along a portion 314 of curve 310 to a point below approximately 3.0 volts (as shown by the dashed portion of curve 310 in FIG. 8).

The potential of the negative electrode decreases from a point below approximately 2.0 volts on initial charging to a point below the decomposition potential of the $LiCoO_2$ active material provided on the positive current collector (designated by dashed line 312 and below the decomposition potential of the secondary or auxiliary active material (designated by dashed line 332)). According to an exemplary embodiment, the corrosion potential of copper is approximately 3.5 volts, while the decomposition potential of the $LiCoO_2$ active material provided on the positive current collector is approximately 1.6 volts. According to another exemplary embodiment, the decomposition potential of the $LiCoO_2$ active material is approximately 1.35 volts.

The irreversible loss of capacity of the battery is shown as a ledge or shelf 324 in curve 320. Upon discharging the battery to a point approaching zero volts, the negative electrode potential follows a path designated by a dashed portion 326 of the curve 320. As the potential of the negative electrode moves above the decomposition potential of the auxiliary active material (designated as dash line 332), the auxiliary electrode is electrically connected to the negative electrode, remaining in electrical contact through complete discharging of the battery cell. Upon recharging the battery, the auxiliary electrode will be electrically disconnected from the negative electrode when the potential of the negative electrode moves below the decomposition potential of the auxiliary active material.

Because the active material on the negative current collector is chosen to have significant charging/discharging capacity below the corrosion potential of the negative current collector and above the decomposition potential of the $LiCoO_2$ primary active material, the zero voltage crossing potential (shown as point 330) is below the corrosion potential of the negative current collector and above the decomposition potential of the $LiCoO_2$ primary active material, thus avoiding corrosion of the negative current collector (and potentially of the battery case or any other battery component in electrical contact or communication with the negative electrode) and any associated loss of battery charging capacity. One advantageous feature of such an arrangement is that the battery may be repeatedly cycled (i.e., charged and discharged) to near-zero-voltage conditions without significant decline in battery performance.

It is intended that a lithium-ion battery such as that described herein may be fully discharged while the materials for both electrodes, including their corresponding current collectors, are stable (e.g., corrosion of the current collectors and/or the decomposition of active material may be avoided, etc.). One potential advantageous feature of such an arrangement is that the occurrence of reduced device functionality (i.e., the need to recharge more frequently) and corrosion of the current collectors and battery case (with the incumbent possibility of leaking potentially corrosive and toxic battery contents) may be reduced or avoided.

While the auxiliary electrode 260 has been described with respect to being selectively electrically connected or coupled to the negative electrode 220, according to another exemplary embodiment, an auxiliary electrode may be provided such that it may be selectively electrically connected or coupled to a positive electrode. FIGS. 9-13 show various views of a battery 600 having a case 602 including a positive electrode 610, a negative electrode 620, and an auxiliary electrode 660 selectively electrically coupled or connected to the positive electrode (e.g., by a switch 670, and according to another exemplary embodiment, according to a diode or other device). Also, it should be noted that one of the positive electrode 610 and negative electrode 620 may be coupled to the case 602 (e.g., as opposed to being electrically isolated from the case) according to other exemplary embodiments. The auxiliary electrode 660, while being shown in the headspace of the battery 600, may be provided in other locations as may be desired. The various components shown in FIGS. 9-13 include reference numerals similar to those shown in FIGS. 3-7, with the reference numerals in FIGS. 9-13 being 400 away from the reference numerals shown in FIGS. 2-7 (e.g., negative electrode 220 shown in FIG. 4 corresponds to negative electrode 620 shown in FIG. 10).

Figure 10:
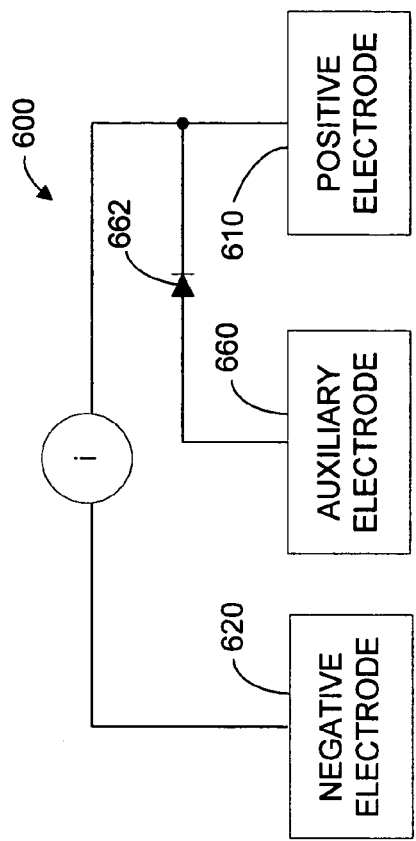
FIG. 10 is a schematic view of the lithium-ion battery shown in FIG. 9 according to one exemplary embodiment.
Figure 11:
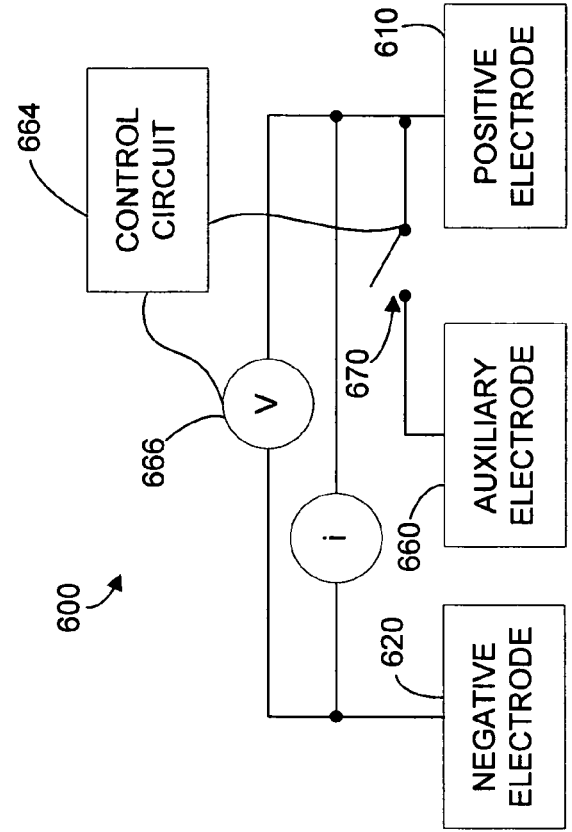
FIG. 11 is a schematic view of the lithium-ion battery shown in FIG. 9 according to another exemplary embodiment.
Figure 9:
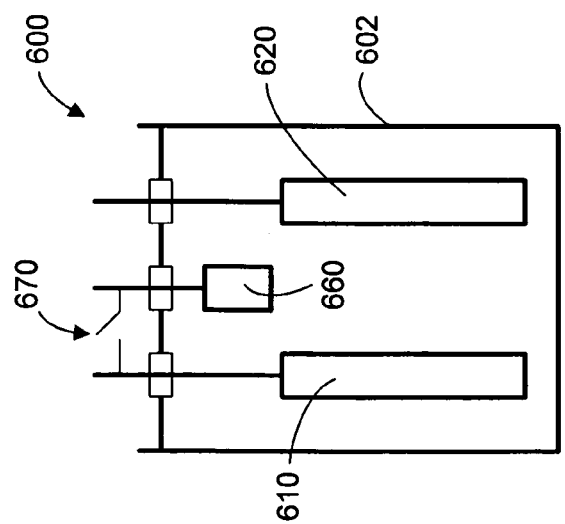
FIG. 9 is a schematic view of a portion of a lithium-ion battery having an auxiliary positive electrode according to an exemplary embodiment.
Figure 12:
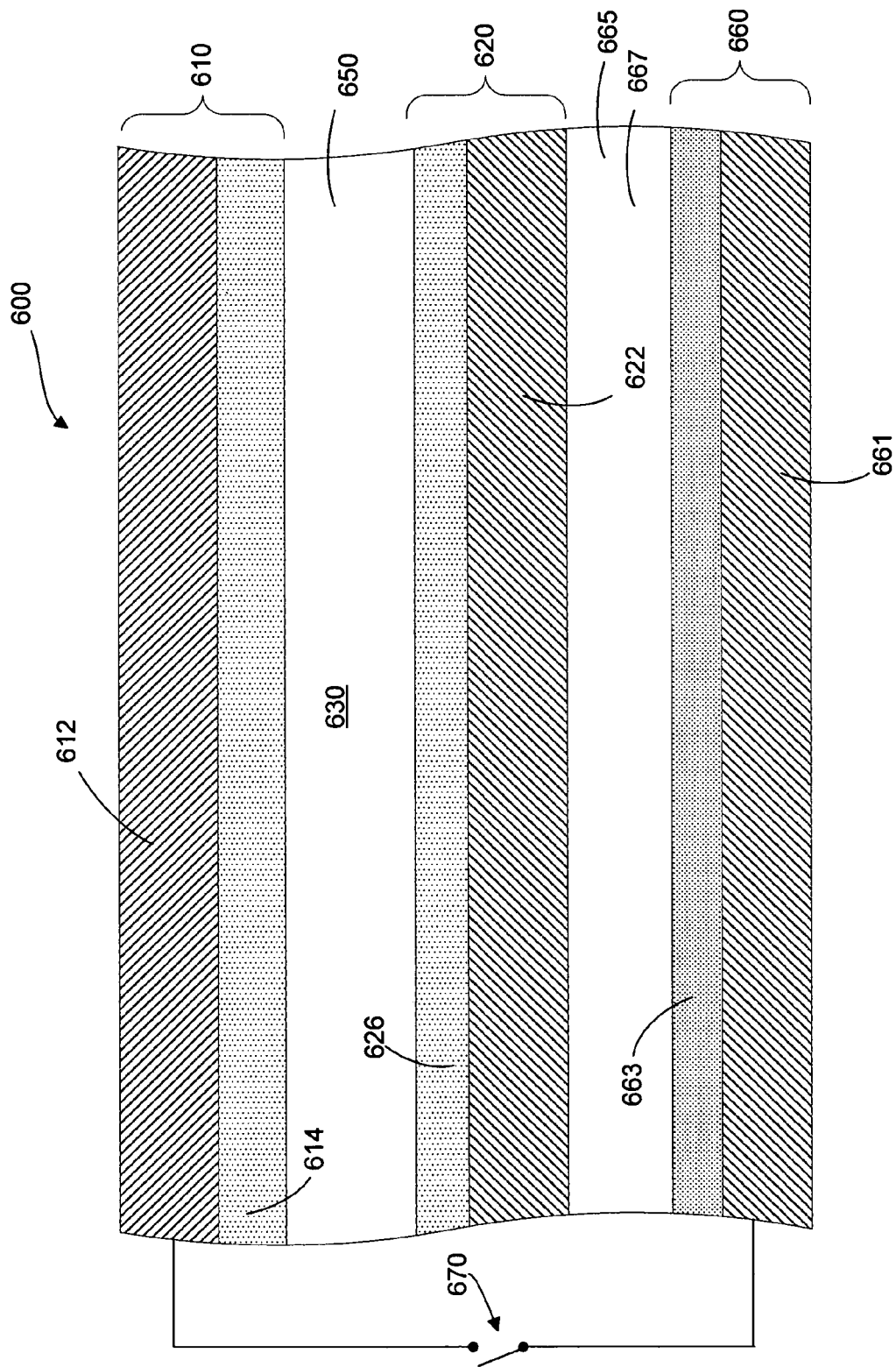
FIG. 12 is a schematic cross-sectional view of a portion of the lithium-ion battery shown in FIG. 9 according to one exemplary embodiment.
Figure 13:
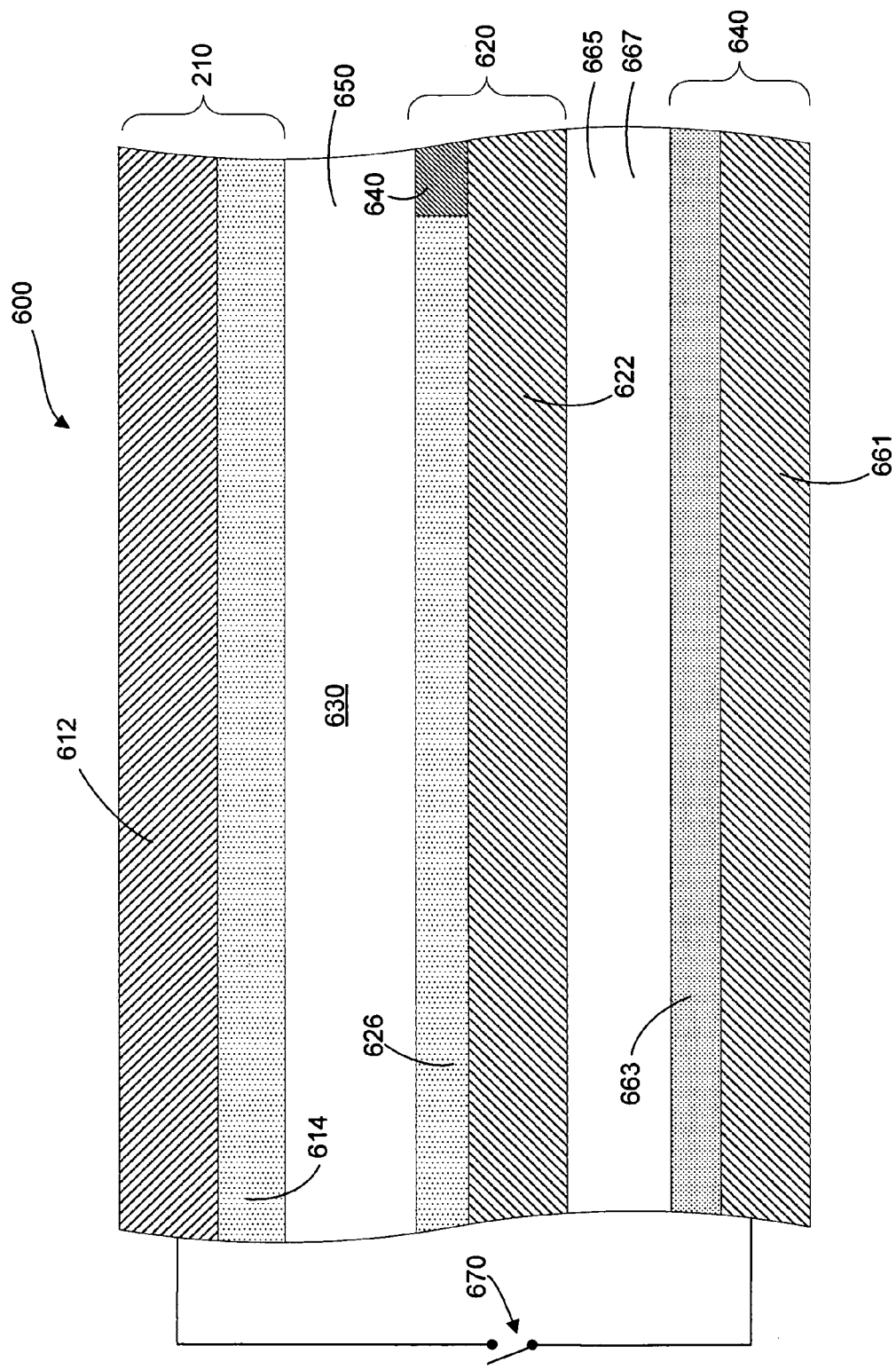
FIG. 13 is a schematic cross-sectional view of a portion of the lithium-ion battery shown in FIG. 9 according to another exemplary embodiment.

FIGS. 10-11 show exemplary schematic views of configurations for exemplary embodiments in which an auxiliary electrode 660 is selectively electrically coupled to a positive electrode 610. Such configurations are similar to those shown in FIGS. 4-5, with FIG. 10 representing the use of a diode 662 and FIG. 11 representing the use of a control circuit 664 which operates to close a switch 670 to electrically connect the auxiliary electrode 660 to the positive electrode 610. As shown in FIGS. 12-13, a switch 670 is provided which electrically connects the positive electrode 610 to the auxiliary electrode 660 external to the battery 600. The auxiliary electrode 660 is electrically isolated (using a separator 665) from both the positive electrode 610 and the negative electrode 620, and an electrolyte 667 may be provided. It should be noted that while FIGS. 12 and 13 show the auxiliary electrode as being adjacent to the negative electrode, the auxiliary electrode may be provided adjacent the positive electrode according to another exemplary embodiment. The various materials used for the components of the battery 600 may be identical to those described with respect to the battery 200.

The active material 663 provided on the current collector 661 of the auxiliary electrode 660 may be formed from a material similar to those described above, with the provision that such materials must be provided in their oxidized (i.e., de-lithiated) form. That is to say, the auxiliary electrode does not include an active material that utilizes lithium according to an exemplary embodiment in which the auxiliary electrode is configured for selective coupling and decoupling from the positive electrode. Further, it should be noted that according to an exemplary embodiment in which the auxiliary electrode is configured for selective coupling and decoupling from the positive electrode, the active material provided on the negative current collector must include lithium or be provided with a source of lithium (e.g., powdered lithium, a lithium patch, etc.) sufficient to compensate at minimum for the loss of lithium due to the formation of an SEI during initial charging (see, e.g., FIG. 12, in which a powdered lithium material is provided, and FIG. 13, in which a lithium patch is provided on the negative electrode).

It may be advantageous to provide a battery such as that shown as battery 600 in FIGS. 9-13 for a variety of reasons. For example, the active material 663 provided on the current collector 661 of the auxiliary electrode 660 may prevent the positive electrode from being pulled below its decomposition potential in a fully discharged cell (e.g., it may prevent decomposition of the active material 614 provided on the current collector 612 of the positive electrode 610). This may protect the positive electrode in situations where, for example, the negative electrode (e.g., a carbon electrode) is pre-lithiated using the lithium patch in order to protect its potential from being pulled above the corrosion potential of the negative current collector 622 of the negative electrode 620. It may also be advantageous to provide a battery having an arrangement such as that shown in FIGS. 9-13 in the event that the active material applied to the auxiliary electrode is not stable (i.e., becomes oxidized) at the maximum potential of the positive electrode in a fully charged cell. In contrast, in situations in which the secondary active material is stable (i.e., does not become oxidized at the maximum potential of the positive electrode in a fully charged cell), it could be directly added to the positive electrode material.

Various advantageous features may be obtained by utilizing batteries such as those shown and described herein. For example, use of such batteries may eliminate the need to utilize circuitry to disconnect batteries approaching near-zero voltage conditions. By not utilizing circuitry for this function, volume and cost reductions may be obtained.

According to an exemplary embodiment, lithium-ion batteries such as those described above may be used in conjunction with medical devices such as medical devices that may be implanted in the human body (referred to as "implantable medical devices" or "IMD's").

Figure 14:
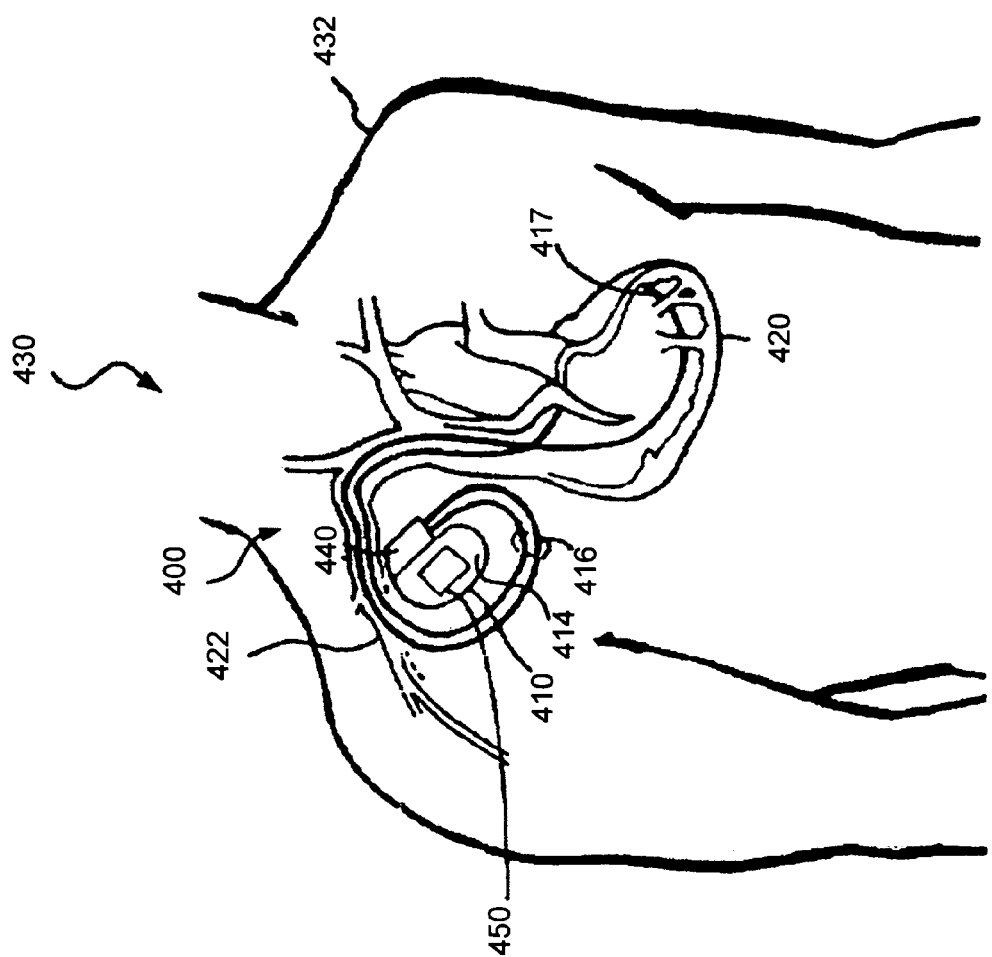
FIG. 14 is a schematic view of a system in the form of an implantable medical device implanted within a body or torso of a patient.

FIG. 14 illustrates a schematic view of a system 400 (e.g., an implantable medical device) implanted within a body or torso 432 of a patient 430. The system 400 includes a device 410 in the form of an implantable medical device that for purposes of illustration is shown as a defibrillator configured to provide a therapeutic high voltage (e.g., 700 volt) treatment for the patient 430.

The device 410 includes a container or housing 414 that is hermetically sealed and biologically inert according to an exemplary embodiment. The container may be made of a conductive material. One or more leads 416 electrically connect the device 410 and to the patient's heart 420 via a vein 422. Electrodes 417 are provided to sense cardiac activity and/or provide an electrical potential to the heart 420. At least a portion of the leads 416 (e.g., an end portion of the leads shown as exposed electrodes 417) may be provided adjacent or in contact with one or more of a ventricle and an atrium of the heart 420.

The device 410 includes a battery 440 provided therein to provide power for the device 410. According to another exemplary embodiment, the battery 440 may be provided external to the device or external to the patient 430 (e.g., to allow for removal and replacement and/or charging of the battery). The size and capacity of the battery 440 may be chosen based on a number of factors, including the amount of charge required for a given patient's physical or medical characteristics, the size or configuration of the device, and any of a variety of other factors. According to an exemplary embodiment, the battery is a 500 mAh battery. According to another exemplary embodiment, the battery is a 300 mAh battery. According to various other exemplary embodiments, the battery may have a capacity of between approximately 10 and 1000 mAh.

According to other exemplary embodiments, more than one battery may be provided to power the device 410. In such exemplary embodiments, the batteries may have the same capacity or one or more of the batteries may have a higher or lower capacity than the other battery or batteries. For example, according to an exemplary embodiment, one of the batteries may have a capacity of approximately 500 mAh while another of the batteries may have a capacity of approximately 75 mAh.

One or more capacitors (shown as capacitor bank 450) are provided in the device to store energy provided by the battery 440. For example, the system 410 may be configured such that when the device 410 determines that a therapeutic high-voltage treatment is required to establish a normal sinus rhythm for the heart 420, the capacitors in the capacitor bank 450 are charged to a predetermined charge level by the battery 440. Charge stored in the capacitors may then be discharged via the leads 416 to the heart 420. According to another exemplary embodiment, the capacitors may be charged prior to determination that a stimulating charge is required by the heart such that the capacitors may be discharged as needed.

Figure 15:
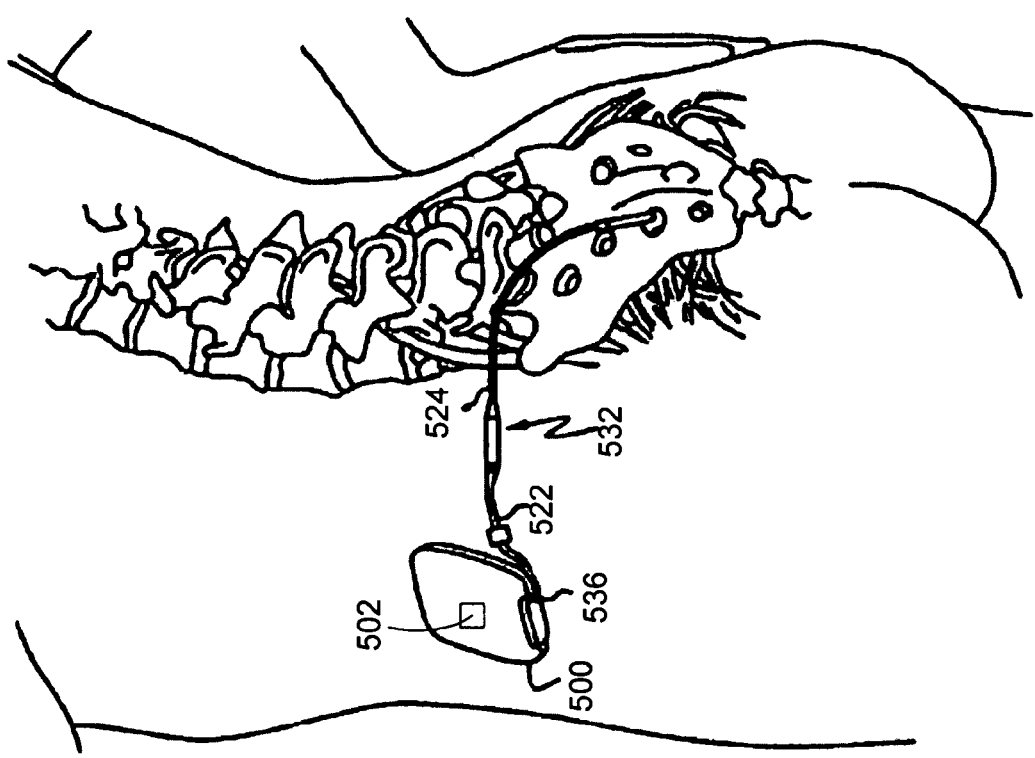
FIG. 15 is schematic view of another system in the form of an implantable medical device.

According to another exemplary embodiment shown in FIG. 15, an implantable neurological stimulation device 500 (an implantable neuro stimulator or INS) may include a battery 502 such as those described above with respect to the various exemplary embodiments. Examples of other neuro stimulation products and related components are shown and described in a brochure titled "Implantable Neurostimulation Systems" available from Medtronic, Inc.

An INS generates one or more electrical stimulation signals that are used to influence the human nervous system or organs. Electrical contacts carried on the distal end of a lead are placed at the desired stimulation site such as the spine or brain and the proximal end of the lead is connected to the INS. The INS is then surgically implanted into an individual such as into a subcutaneous pocket in the abdomen, pectoral region, or upper buttocks area. A clinician programs the INS with a therapy using a programmer. The therapy configures parameters of the stimulation signal for the specific patient's therapy. An INS can be used to treat conditions such as pain, incontinence, movement disorders such as epilepsy and Parkinson's disease, and sleep apnea. Additional therapies appear promising to treat a variety of physiological, psychological, and emotional conditions. Before an INS is implanted to deliver a therapy, an external screener that replicates some or all of the INS functions is typically connected to the patient to evaluate the efficacy of the proposed therapy.

The INS 500 includes a lead extension 522 and a stimulation lead 524. The stimulation lead 524 is one or more insulated electrical conductors with a connector 532 on the proximal end and electrical contacts (not shown) on the distal end. Some stimulation leads are designed to be inserted into a patient percutaneously, such as the Model 3487A Pisces-Quad® lead available from Medtronic, Inc. of Minneapolis Minn., and stimulation some leads are designed to be surgically implanted, such as the Model 3998 Specify® lead also available from Medtronic.

Although the lead connector 532 can be connected directly to the INS 500 (e.g., at a point 536), typically the lead connector 532 is connected to a lead extension 522. The lead extension 522, such as a Model 7495 available from Medtronic, is then connected to the INS 500.

Implantation of an INS 520 typically begins with implantation of at least one stimulation lead 524, usually while the patient is under a local anesthetic. The stimulation lead 524 can either be percutaneously or surgically implanted. Once the stimulation lead 524 has been implanted and positioned, the stimulation lead's 524 distal end is typically anchored into position to minimize movement of the stimulation lead 524 after implantation. The stimulation lead's 524 proximal end can be configured to connect to a lead extension 522.

The INS 500 is programmed with a therapy and the therapy is often modified to optimize the therapy for the patient (i.e., the INS may be programmed with a plurality of programs or therapies such that an appropriate therapy may be administered in a given situation). In the event that the battery 502 requires recharging, an external lead (not shown) may be used to electrically couple the battery to a charging device or apparatus.

A physician programmer and a patient programmer (not shown) may also be provided to allow a physician or a patient to control the administration of various therapies. A physician programmer, also known as a console programmer, uses telemetry to communicate with the implanted INS 500, so a clinician can program and manage a patient's therapy stored in the INS 500, troubleshoot the patient's INS 500 system, and/or collect data. An example of a physician programmer is a Model 7432 Console Programmer available from Medtronic. A patient programmer also uses telemetry to communicate with the INS 500, so the patient can manage some aspects of her therapy as defined by the clinician. An example of a patient programmer is a Model 7434 Itrel® 3 EZ Patient Programmer available from Medtronic.

While the medical devices described herein (e.g., systems 400 and 500) are shown and described as a defibrillator and a neurological stimulation device, it should be appreciated that other types of implantable medical devices may be utilized according to other exemplary embodiments, such as pacemakers, cardiac contractility modulators, cardioverters, drug administering devices, diagnostic recorders, cochlear implants, and the like for alleviating the adverse effects of various health ailments. According to still other embodiments, non-implantable medical devices or other types of devices may utilize batteries as are shown and described in this disclosure.

It is also contemplated that the medical devices described herein may be charged or recharged when the medical device is implanted within a patient. That is, according to an exemplary embodiment, there is no need to disconnect or remove the medical device from the patient in order to charge or recharge the medical device. For example, transcutaneous energy transfer (TET) may be used, in which magnetic induction is used to deliver energy from outside the body to the implanted battery, without the need to make direct physical contact to the implanted battery, and without the need for any portion of the implant to protrude from the patient's skin. According to an exemplary embodiment, a connector may be provided external to the patient's body that may be electrically coupled to a charging device in order to charge or recharge the battery. According to other exemplary embodiments, medical devices may be provided that may require removal or detachment from the patient in order to charge or recharge the battery.

It should be understood that while the present disclosure describes the use of lithium-ion batteries with a variety of medical devices, such batteries may be used in a variety of other applications, including computers (e.g., laptop computers), phones (e.g., cellular, mobile, or cordless phones), automobiles, and any other device or application for which it may be advantageous to provide power in the form of a lithium-ion battery.

It is also important to note that the construction and arrangement of the lithium-ion battery as shown and described with respect to the various exemplary embodiments is illustrative only. Although only a few embodiments of the present inventions have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited in the claims. Accordingly, all such modifications are intended to be included within the scope of the present invention as defined in the appended claims. Other substitutions, modifications, changes and omissions may be made in the design, operating conditions and arrangement of the preferred and other exemplary embodiments without departing from the scope of the present invention as expressed in the appended claims.

What is claimed is:

1. A medical device comprising:
a rechargeable lithium-ion battery for providing power to the medical device, the lithium-ion battery comprising:
a positive electrode comprising a current collector and a first active material;
a negative electrode comprising a current collector and a second active material; and
an auxiliary electrode comprising a current collector and a third active material, the auxiliary electrode adapted for repeated electrical connection to the positive and negative electrodes, but the auxiliary electrode being connected to only one of the positive electrode and the negative electrode at any one point in time and when selectively connected;
wherein the first active material, second active material, and third active material are configured to allow doping and undoping of lithium-ions; and
wherein the third active material exhibits charging and discharging capacity below a corrosion potential of the current collector of the negative electrode and above a decomposition potential of the first active material.

2. The medical device of claim 1, wherein at least a portion of the medical device is configured for implantation into a body of a patient.

3. The medical device of claim 2, wherein a portion of the medical device including the lithium-ion battery is implanted into the body of the patient, wherein the lithium-ion battery may be charged without removing the battery from the body of the patient.

4. The medical device of claim 1, wherein the medical device comprises a neurological stimulation device.

5. The medical device of claim 4, wherein the neurological stimulation device is configured to provide a therapeutic treatment to a patient by electrically stimulating a portion of at least one of a patient's brain and a patient's spine.

6. The medical device of claim 5, wherein the neurological stimulation device is programmed to selectively provide a plurality of therapeutic treatments to a patient.

7. The medical device of claim 1, wherein the medical device is selected from the group consisting of a cardiac defibrillator, a cardiac pacemaker, a cardiac contractility modulator, a cardioverter, a drug administration device, a cochlear implant, a hearing aid, a sensor, a telemetry device, and a diagnostic recorder.

8. The medical device of claim 7, wherein the device is an implantable cardiac defibrillator for providing a therapeutic high voltage treatment to a patient.

9. The medical device of claim 1, wherein the auxiliary electrode is provided such that it is electrically isolated from the positive electrode and the negative electrode within the battery.

10. The medical device of claim 9, wherein the auxiliary electrode is configured to be selectively electrically connected to and disconnected from one of the positive electrode and the negative electrode using a mechanism provided external to the battery.

11. The medical device of claim 1, wherein the auxiliary electrode is configured to be selectively electrically connected to and disconnected from one of the positive electrode and the negative electrode using a diode.

12. The medical device of claim 11, wherein the battery is configured to electrically connect the auxiliary electrode to the negative electrode when the potential of the negative electrode exceeds the potential of the auxiliary electrode by a predetermined value.

13. The medical device of claim 11, wherein the battery is configured to electrically connect the auxiliary electrode to the positive electrode when the potential of the positive electrode falls below the potential of the auxiliary electrode by a predetermined value.

14. The medical device of claim 1, wherein the auxiliary electrode is configured to be selectively electrically connected to and disconnected from one of the positive electrode and the negative electrode using a switch.

15. The medical device of claim 14, wherein the switch is configured to selectively electrically connect the auxiliary electrode when the difference in voltage between the positive electrode and the negative electrode falls below a predetermined value.

16. The medical device of claim 14, wherein the switch is configured to selectively electrically disconnect the auxiliary electrode when the difference in voltage between the positive electrode and the negative electrode exceeds a predetermined value.

17. The medical device of claim 1, wherein the auxiliary electrode is configured for selective electrical coupling to the negative electrode.

18. The medical device of claim 17, further comprising a source of lithium in electrical contact with the auxiliary electrode.

19. The medical device of claim 18, wherein the source of lithium comprises at least one of a lithium patch and powdered lithium.

20. The medical device of claim 17, wherein the third active material comprises electrochemically active lithium.

21. The medical device of claim 20, wherein the third active material comprises a material selected from the group consisting of $LiMn_2O_4$, $Li_xVO_2$, $LiM_xMn_{(2-x)}O_4$ (where M is a metal), and combinations thereof.

22. The medical device of claim 1, wherein the auxiliary electrode is configured for selective electrical connection to the positive electrode.

23. The medical device of claim 22, wherein the third active material does not include electrochemically active lithium.

24. The medical device of claim 23, wherein second active material comprises a lithium titanate material.

25. The medical device of claim 23, further comprising a source of lithium in electrical contact with the negative electrode.

26. The medical device of claim 25, wherein the source of lithium comprises at least one of a lithium patch and powdered lithium.

27. The medical device of claim 26, wherein the source of lithium is configured to provide a lithium capacity for the negative electrode sufficient to at least compensate for irreversible loss of capacity of the negative electrode.

28. The medical device of claim 23, wherein the third active material comprises a material selected from the group consisting of $V_2O_5$, $V_6O_{13}$, $V_3O_8$, $MoO_3$, $TiS_2$, $WO_2$, $MoO_2$, $RuO_2$, and combinations thereof.

29. The medical device of claim 1, wherein the first active material comprises a material selected from the group consisting of $LiCoO_2$, a material having the form $LiCo_xNi_{(1-x)}O_2$, a material having the form $LiCo_xMn_yNi_zO_2$, and a material having the form $LiNi_xCo_yAl_zO_2$.

30. The medical device of claim 1, further comprising a polymeric separator provided intermediate the positive electrode and the negative electrode.

31. The medical device of claim 1, wherein the battery has a capacity between approximately 10 mAh and 1000 mAh.

32. A medical device comprising:
a rechargeable lithium-ion battery for providing power to the medical device, the lithium-ion battery comprising:
a positive electrode comprising a current collector and a first active material;
a negative electrode comprising a current collector and a second active material; and
an auxiliary electrode comprising a current collector and a third active material, the auxiliary electrode configured for repeated, selective electrical connections to the negative electrode when the potential of the negative electrode exceeds the potential of the auxiliary electrode by a predetermined value, the third active material providing excess capacity to the negative electrode when the auxiliary electrode is electrically connected to the negative electrode;
wherein the first active material, second active material, and third active material are configured to allow doping and undoping of lithium-ions; and
wherein the third active material exhibits charging and discharging capacity below a corrosion potential of the current collector of the negative electrode and above a decomposition potential of the first active material.

33. The medical device of claim 32, wherein at least a portion of the medical device is configured for implantation into a body of a patient.

34. The medical device of claim 33, wherein a portion of the medical device including the lithium-ion battery is implanted into the body of the patient, wherein the lithium-ion battery may be charged without removing the battery from the body of the patient.

35. The medical device of claim 32, wherein the medical device comprises a neurological stimulation device.

36. The medical device of claim 35, wherein the neurological stimulation device is configured to provide a therapeutic treatment to a patient by electrically stimulating a portion of at least one of a patient's brain and a patient's spine.

37. The medical device of claim 36, wherein the neurological stimulation device is programmed to selectively provide a plurality of therapeutic treatments to a patient.

38. The medical device of claim 32, wherein the medical device is selected from the group consisting of a cardiac defibrillator, a cardiac pacemaker, a cardiac contractility modulator, a cardioverter, a drug administration device, a cochlear implant, a hearing aid, a sensor, a telemetry device, and a diagnostic recorder.

39. The medical device of claim 38, wherein the device is an implantable cardiac defibrillator for providing a therapeutic high voltage treatment to a patient.

40. The medical device of claim 32, wherein the auxiliary electrode is provided such that it is electrically isolated from the positive electrode and the negative electrode within the battery.

41. The medical device of claim 40, wherein the auxiliary electrode is configured to be selectively electrically connected to and disconnected from the negative electrode using a mechanism provided external to the battery.

42. The medical device of claim 32, wherein the auxiliary electrode is configured to be selectively electrically connected to and disconnected from the negative electrode using a diode.

43. The medical device of claim 32, wherein the auxiliary electrode is configured to be selectively electrically connected to and disconnected from the negative electrode using a switch.

44. The medical device of claim 43, wherein the switch is configured to selectively electrically connect the auxiliary electrode when the difference in voltage between the positive electrode and the negative electrode falls below a predetermined value.

45. The medical device of claim 43, wherein the switch is configured to selectively electrically disconnect the auxiliary electrode when the difference in voltage between the positive electrode and the negative electrode exceeds a predetermined value.

46. The medical device of claim 32, further comprising a source of lithium in electrical contact with the auxiliary electrode.

47. The medical device of claim 46, wherein the source of lithium comprises at least one of a lithium patch and powdered lithium.

48. The medical device of claim 32, wherein the third active material comprises electrochemically active lithium.

49. The medical device of claim 48, wherein the third active material comprises a material selected from the group consisting of $LiMn_2O_4$, $Li_xVO_2$, $LiM_xMn_{(2-x)}O_4$ (where M is a metal), and combinations thereof.

50. The medical device of claim 32, wherein the first active material comprises a material selected from the group consisting of $LiCoO_2$, a material having the form $LiCo_xNi_{(1-x)}O_2$, a material having the form $LiCo_xMn_yNi_zO_2$, and a material having the form $LiNi_xCo_yAl_zO_2$.

51. The medical device of claim 32, further comprising a polymeric separator provided intermediate the positive electrode and the negative electrode.

52. The medical device of claim 32, wherein the battery has a capacity between approximately 10 mAh and 1000 mAh.

53. A medical device comprising:
a rechargeable lithium-ion battery for providing power to the medical device, the lithium-ion battery comprising:
a positive electrode comprising a current collector and a first active material;
a negative electrode comprising a current collector and a second active material; and
an auxiliary electrode comprising a current collector and a third active material, the auxiliary electrode configured for repeated, selective electrical connections to the positive electrode when the potential of the positive electrode falls below the potential of the auxiliary electrode by a predetermined value, the third active material providing excess capacity to the positive electrode when the auxiliary electrode is electrically connected to the positive electrode;
wherein the first active material, second active material, and third active material are configured to allow doping and undoping of lithium-ions; and
wherein the third active material exhibits charging and discharging capacity below a corrosion potential of the current collector of the negative electrode and above a decomposition potential of the first active material.

54. The medical device of claim 53, wherein at least a portion of the medical device is configured for implantation into a body of a patient.

55. The medical device of claim 54, wherein a portion of the medical device including the lithium-ion battery is implanted into the body of the patient, wherein the lithium-ion battery may be charged without removing the battery from the body of the patient.

56. The medical device of claim 53, wherein the medical device comprises a neurological stimulation device.

57. The medical device of claim 56, wherein the neurological stimulation device is configured to provide a therapeutic treatment to a patient by electrically stimulating a portion of at least one of a patient's brain and a patient's spine.

58. The medical device of claim 57, wherein the neurological stimulation device is programmed to selectively provide a plurality of therapeutic treatments to a patient.

59. The medical device of claim 53, wherein the medical device is selected from the group consisting of a cardiac defibrillator, a cardiac pacemaker, a cardiac contractility modulator, a cardioverter, a drug administration device, a cochlear implant, a hearing aid, a sensor, a telemetry device, and a diagnostic recorder.

60. The medical device of claim 59, wherein the device is an implantable cardiac defibrillator for providing a therapeutic high voltage treatment to a patient.

61. The medical device of claim 53, wherein the auxiliary electrode is provided such that it is electrically isolated from the positive electrode and the negative electrode within the battery.

62. The medical device of claim 61, wherein the auxiliary electrode is configured to be selectively electrically connected to and disconnected from the positive electrode using a mechanism provided external to the battery.

63. The medical device of claim 53, wherein the auxiliary electrode is configured to be selectively electrically connected to and disconnected from the positive electrode using a diode.

64. The medical device of claim 53, wherein the battery is configured to electrically connect the auxiliary electrode to the positive electrode when the potential of the positive electrode falls below the potential of the auxiliary electrode by a predetermined value.

65. The medical device of claim 53, wherein the auxiliary electrode is configured to be selectively electrically connected to and disconnected from the positive electrode using a switch.

66. The medical device of claim 65, wherein the switch is configured to selectively electrically connect the auxiliary electrode when the difference in voltage between the positive electrode and the negative electrode falls below a predetermined value.

67. The medical device of claim 65, wherein the switch is configured to selectively electrically disconnect the auxiliary electrode when the difference in voltage between the positive electrode and the negative electrode exceeds a predetermined value.

68. The medical device of claim 53, wherein the third active material does not include electrochemically active lithium.

69. The medical device of claim 68, wherein second active material comprises a lithium titanate material.

70. The medical device of claim 68, further comprising a source of lithium in electrical contact with the negative electrode.

71. The medical device of claim 70, wherein the source of lithium comprises at least one of a lithium patch and powdered lithium.

72. The medical device of claim 71, wherein the source of lithium is configured to provide a lithium capacity for the negative electrode sufficient to at least compensate for irreversible loss of capacity of the negative electrode.

73. The medical device of claim 68, wherein the third active material comprises a material selected from the group consisting of $V_2O_5$, $V_6O_{13}$, $V_3O_8$, $MoO_3$, $TiS_2$, $WO_2$, $MoO_2$, $RuO_2$, and combinations thereof.

74. The medical device of claim 53, wherein the first active material comprises a material selected from the group consisting of $LiCoO_2$, a material having the form $LiCo_xNi_{(1-x)}O_2$, a material having the form $LiCo_xMn_yNi_zO_2$, and a material having the form $LiNi_xCo_yAl_zO_2$.

75. The medical device of claim 53, further comprising a polymeric separator provided intermediate the positive electrode and the negative electrode.

76. The medical device of claim 53, wherein the battery has a capacity between approximately 10 mAh and 1000 mAh.

* * * * *

UNITED STATES PATENT AND TRADEMARK OFFICE
CERTIFICATE OF CORRECTION

PATENT NO. : 7,641,992 B2
APPLICATION NO. : 10/978970
DATED : January 5, 2010
INVENTOR(S) : Howard et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1088 days.

Signed and Sealed this

Twenty-first Day of December, 2010

David J. Kappos
*Director of the United States Patent and Trademark Office*